United States Patent
Butler et al.

(10) Patent No.: US 8,987,322 B2
(45) Date of Patent: Mar. 24, 2015

(54) PHARMACEUTICAL FORMULATIONS FOR CARRIER-MEDIATED TRANSPORT STATINS AND USES THEREOF

(75) Inventors: Jackie Butler, Athlone (IE); John Devane, Athlone (IE); Paul Stark, Athlone (IE)

(73) Assignee: Circ Pharma Research and Development Limited, Dublin (IE)

( * ) Notice: Subject to any disclaimer, the term of this patent is extended or adjusted under 35 U.S.C. 154(b) by 1782 days.

(21) Appl. No.: 10/967,167

(22) Filed: Oct. 19, 2004

(65) Prior Publication Data
US 2005/0119331 A1 Jun. 2, 2005

Related U.S. Application Data

(60) Provisional application No. 60/516,770, filed on Nov. 4, 2003.

(51) Int. Cl.
| | |
|---|---|
| A61K 31/40 | (2006.01) |
| A61K 9/28 | (2006.01) |
| A61K 9/20 | (2006.01) |
| A61K 31/505 | (2006.01) |
| C07D 207/34 | (2006.01) |

(52) U.S. Cl.
CPC .............. *A61K 9/2846* (2013.01); *A61K 9/2054* (2013.01); *A61K 9/284* (2013.01); *A61K 31/40* (2013.01); *A61K 31/505* (2013.01); *C07D 207/34* (2013.01); *A61K 9/2018* (2013.01)
USPC ............ 514/423; 514/427; 514/708; 548/537

(58) Field of Classification Search
CPC . A61K 31/401; A61K 9/2072; A61K 9/2004; A61K 31/216
USPC .......................................... 514/423; 424/468
See application file for complete search history.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 4,088,864 | A | 5/1978 | Theeuwes et al. |
| 4,200,098 | A | 4/1980 | Ayer et al. |
| 4,557,925 | A | 12/1985 | Lindahl et al. |
| 4,803,081 | A * | 2/1989 | Falk et al. ................. 424/488 |
| 4,904,474 | A * | 2/1990 | Theeuwes et al. ......... 424/424 |
| 5,573,776 | A | 11/1996 | Harrison et al. |
| 6,248,363 | B1 * | 6/2001 | Patel et al. ................. 424/497 |
| 6,498,156 | B2 * | 12/2002 | Glombik et al. ....... 514/210.02 |
| 6,569,461 | B1 * | 5/2003 | Tillyer et al. ............. 424/497 |
| 6,881,860 | B2 * | 4/2005 | Luchoomun et al. ...... 562/426 |
| 2002/0147232 | A1 * | 10/2002 | Sundgreen et al. ........ 514/474 |
| 2002/0183527 | A1 * | 12/2002 | Pflaum ....................... 548/530 |
| 2003/0124191 | A1 * | 7/2003 | Besse et al. ................ 424/489 |

FOREIGN PATENT DOCUMENTS

| | | |
|---|---|---|
| EP | 0465096 | 1/1992 |
| WO | 0021525 | 4/2000 |
| WO | 0053173 | 9/2000 |
| WO | 03057195 | 7/2003 |
| WO | 2004021972 | 3/2004 |
| WO | 2004021973 | 3/2004 |

OTHER PUBLICATIONS

U.S. Pharmacopeia, (2002), Solubility definitions.
Malinowski, J. (1998) Am J Health-Syst Pharm 55:2253.
A Treatise on Controlled Drug Delivery, Fundamentals, Optimization and Applications, 1991.
Lehmann, K.O.R., Chemistry and Application Properties of Polymethacrylate Coating Systems, in Aqueous Polymeric Coatings for Pharmaceutical Dosage Forms, McGinty, J. W., ed. pp. 109-114, 1997.
Michael Igel et al., "Pharmacology of 3-Hydroxy-3-Methylglutaryl-Coenzyme A Reductase Inhibitors (Statins), Including Rosuvastatin and Pitavastatin," *J. Clin harmacol*, 2002; 42:835-845.
Joseph Triscari, PhD. et al., "Gastrointestinal Absorption of Pravastatin in Healthy Subjects," *J Clin Pharmacol*, 1995;35:142-144.
Angela Cheng-Lai, "Rosuvastatin: A New HMG-CoA Reductase Inhibitor for the Treatment of Hypercholesterolemia," *Heart Disease*, 2003;5:72-78.
C. Michael White, "A Review of the Pharmacologic and Pharmacokinetic Aspects of Rosuvastatin," *J Clin Pharmacol*, 2002;42:963-970.
G.C. Santus et al., "Transdermal enhancer patent literature," *Journal of Controlled Release*, 25 (1993) 1-20.
Handbook of Pharmaceutical Controlled Release Technology Table of Contents, 2000.

\* cited by examiner

*Primary Examiner* — James D Anderson
*Assistant Examiner* — Meghan Finn
(74) *Attorney, Agent, or Firm* — Fox Rothschild LLP

(57) ABSTRACT

The present invention relates to formulations comprising therapeutically effective amounts of at least one acid-stable, carrier-mediated transport statin, at least one poorly water-soluble, carrier-mediated transport statin, or at least one large molecular weight, carrier-mediated transport statin, such as atorvastatin and rosuvastatin, or a pharmaceutically acceptable salt thereof, and methods of their use. The present formulations and methods are designed to exhibit a controlled-release of a therapeutic amount of the statin in the small intestine, thereby limiting systemic exposure of the statin and maximizing liver-specific absorption of the drug. The formulations and methods of the present invention are particularly useful for treating and/or preventing conditions that are benefited by decreasing levels of lipids and/or cholesterol in the body.

8 Claims, No Drawings

PHARMACEUTICAL FORMULATIONS FOR CARRIER-MEDIATED TRANSPORT STATINS AND USES THEREOF

This application claims the benefit of priority of U.S. Provisional Application No. 60/516,770, filed Nov. 4, 2003, which is incorporated by reference herein.

FIELD OF THE INVENTION

The present invention relates to pharmaceutical formulations and methods of their use. In particular, it relates to formulations of, and methods of using, statins that are absorbed through the intestine and subsequently in the liver via carrier-mediated transport mechanisms, and are also either stable in an acidic environment, have poor membrane permeability due to their large molecular size, and/or have poor water solubility. The transport properties of these statins, as well as other physical characteristics, limit their hepatic bioavailability. The statin formulations of the present invention address the problems associated with these characteristics, and result in increased hepatic bioavailability.

BACKGROUND OF THE INVENTION

Statins are a class of compounds that competitively inhibit 3-hydroxy-3-methylglutaryl-co-enzyme A (HMG-CoA) reductase, which catalyzes the conversion of HMG-CoA to mevalonate, an early rate-limiting step in cholesterol biosynthesis (Igel et al. (2002) *J. Clin. Pharmacol.* 42:835). Statins lower blood lipid levels by reducing cholesterol biosynthesis in the liver. Accordingly, statins are known for their ability to help reduce levels of total cholesterol and low-density-lipoprotein cholesterol, which is of primary importance in preventing coronary heart disease. Id. Because of possible unwanted effects in non-liver tissues, systemic availability of statins is considered undesirable. Furthermore, to increase the level of HMG-CoA reductase inhibition, it is desirable to maximize hepatic bioavailability.

Certain statins possess properties that limit their hepatic bioavailability, thus decreasing their therapeutic effect and potentially increasing their systemic exposure. The inability to cross biological membranes by diffusion, for example, is one such property. Following ingestion, statins are absorbed through the intestine into the hepatic portal vein and distributed into the liver, which is the primary site of action and the primary site of cholesterol synthesis. Statin compounds that are hydrophilic, lipophobic, and/or have high molecular weights often show poor diffusive permeability across biological membranes in vivo. Accordingly, transport across biological membranes is only possible via a carrier-mediated transport mechanism that typically requires energy, often supplied by the hydrolysis of ATP.

One particular route of statin uptake involves absorption through the small intestine by a carrier-mediated transport mechanism, followed by absorption into hepatocytes, also via a carrier-mediated transport mechanism. Access to the site of action of drugs that are dependent on such carrier-mediated mechanisms depends to a large extent on the capacity of the transport mechanism across the membrane. In the intestine, if a statin is present in an amount that exceeds the capacity of the transport mechanism, the excess drug will be excreted. In the hepatic portal vein, if a statin is present in an amount that saturates the rate of transfer across the membrane, the excess is available for systemic exposure and non-hepatic tissue distribution, and can be detected in the blood.

Another property that can affect hepatic bioavailability is stability in an acidic environment. For example, certain of the statin compounds, such as pravastatin, are unstable in an acidic environment. Triscari et al. (1995) *J. Clin. Pharmacol.* 35:142. If administered by mouth, these statins can undergo non-enzymatic conversion in the stomach to relatively inactive metabolites. Id. To avoid this problem, a protective coating is typically used to delay the release of the statin until it has passed from the acidic environment of the stomach into the small intestine. For acid-stable statins, a protective coating is not required, but may be used as an additional control mechanism in a modified-release formulation. Thus, there is greater flexibility in achieving increased hepatic bioavailability through a modified-release formulation when acid-stable statins are used.

A further property that can limit the hepatic bioavailability of statins is water solubility. Some statin drugs are poorly water-soluble. Statins that are not soluble in water often have poor dissolution profiles, resulting in reduced bioavailbility when administered in vivo. The lack of good water-solubility properties of these drugs creates formulation difficulties that need to be addressed to improve their effectiveness.

A further property that can limit the hepatic bioavailability of certain statins is membrane diffusive permeability. A drug's difficulty in diffusing across biological membranes has a significant impact on drug absorption. Poor membrane permeability can be due to several factors, including the molecular size and charge of the molecule, as well as its hydrophobic/hydrophilic nature. For example, several statins exhibit poor or negligible membrane diffusive permeability due to their large molecular size, and thus rely effectively on being released at the sites of the carrier-mediated transport mechanisms to achieve absorption across biological membranes. In some instances, the limited membrane permeability results in variable or incomplete hepatic bioavailability. Further, even for poorly membrane-diffusive permeable statins that have acceptable oral bioavailability, the rate of absorption is slow and may affect the time to onset of action.

In addition, some statins show an acceptable rate and extent of absorption in the upper gastrointestinal tract, but only if the drug is released in the optimal region of the gastrointestinal tract. For this category of statins, while there may be a therapeutic benefit to altering the time course of drug absorption and systemic exposure after oral administration, the application of conventional controlled-release technology will not achieve the required extent of absorption because the natural site of absorption has been bypassed.

Thus, for statins that display one or more of these properties, which limit their hepatic bioavailability and may also increase their systemic exposure, there exists a need in the art for new formulations that allow for more optimal absorption in the intestine and in the liver. In particular, there is a need for acid stable, carrier-mediated transport statin formulations that provide release rates that maximize absorption in the intestine and in the liver. There also is a need for modified-release formulations that improve the hepatic bioavailibility of poorly water-soluble statins by improving their solubility, and that improve the hepatic bioavailability of large molecular weight statins by improving their permeability. Such modified-release formulations would help maximize statin absorption in the intestine and liver, and thus limit systemic exposure and the associated side effects.

Examples of specific carrier-mediated transport statins that display the properties of acid stability, poor water solubility, and large molecular weight discussed above include atorvastatin and rosuvastatin. Atorvastatin is a member of the statin drug class and is a fully synthetic pentasubstituted pyrrole that is stable in acidic environments. Because of its large molecular size (MW 1209 as the bis calcium salt; MW 557 as the free acid), atorvastatin shows poor membrane permeability, despite its lipophilic character. Atorvastatin is also poorly water-soluble, particularly in acidic environments. For example, as defined in the U.S. Pharmacopeia (2002), atorvastatin is considered "very slightly soluble."

Atorvastatin calcium (sold as LIPITOR®) is thought to share the same mechanism in the liver as other statins through competitive inhibition of HMG-CoA reductase. Accordingly, atorvastatin is generally prescribed for reducing total cholesterol and low-density-lipoprotein cholesterol (LDL-C), which are primary targets in preventing coronary heart disease. Atorvastatin is particularly effective in reducing LDL-C levels (40-60% reduction) compared to other statins (25-35% reduction) (Malinowski (1998) *Am J. Health-Syst Pharm* 55:2253). In addition, atorvastatin appears to reduce levels of triglycerides more than other statins, although the mechanism has not been identified. Id. Atorvastatin is also more effective than other statins in reducing LDL-C in patients with homozygous familial hypercholesterolemia, a rare lipid disorder characterized by an inability to produce functional LDL receptors. Among other actions, atorvastatin also reduces the number of atherosclerotic lesions and reduces vascular smooth muscle cell proliferation. Malinowski (1998) *Am. J. Health-Syst Pharm.* 55:2253.

Unlike acid-unstable statins such as pravastatin, atorvastatin is stable in acidic environments like that found in the stomach. As with all carrier-mediated transport statins, once atorvastatin passes out of the stomach, it is absorbed in the intestine and then in the liver via carrier-mediated transport mechanisms. Only about 30% of orally administered atorvastatin is absorbed from the intestine. Similar to most other statins, atorvastatin undergoes extensive first-pass metabolism in the liver. About 70% or more of the atorvastatin absorbed from the intestine is taken up by the liver, resulting in a systemic bioavailability of the parent drug of approximately 12% and resulting in a systemic availability of active inhibitors (including the parent drug and its metabolites) of 30%. Id. Daily doses of more than 80 mg are not recommended. Peak plasma levels of atorvastatin are achieved 1 to 4 hours following ingestion, while steady-state plasma levels are attained in 32-72 hours. Id. When taken with food, the rate of absorption of atorvastatin is reduced ($C_{max}$ is reduced by 50% and $t_{max}$ delayed by 10 hours), although the overall extent of absorption is only reduced slightly (area under the concentration curve (AUC) is reduced by only 12%). Id.

Several metabolites of atorvastatin appear to show HMG-CoA reductase inhibitory activity that is similar to that of the parent drug. These metabolites, which include o-hydroxylated and p-hydroxylated products, account for approximately 70% of atorvastatin's inhibitory activity. Atorvastatin and its metabolites, as with other statins, are excreted through the bile and are not recirculated through the liver or intestine. The half-life ($t_{1/2}$) of atorvastatin in the plasma ranges from 13-24 hours, and has a mean value of 14 hours. Although the half-life of atorvastatin is less than 24 hours, it is normally administered only once per day since the duration of HMG-CoA reductase inhibition is approximately 20-30 hours due to the inhibitory activity of metabolites. This long-lasting inhibition of atorvastatin may explain the observed increased reduction in lipid levels (Malinowski (1998) *Am J. Health-Syst Pharm* 55:2253).

Rosuvastatin is another new member of the statin family that is stable in acid and whose uptake is governed by carrier-mediated transport mechanisms. Rosuvastatin (which recently received FDA approval under the name CRESTOR®) is a fully synthetic single enantiomeric hydroxy acid, which belongs to a novel series of N-methanesulfonamide pyrimidine and N-methanesulfonyl pyrrole-substituted 3,5-dihydroxy-6-heptenoates (Cheng-Lai (2003) *Heart Disease* 5:72). Although rosuvastatin shares the common statin pharmacophore, it has an additional methane-sulfonamide group that increases its hydrophilicity. Because of its increased hydrophilic character and its large molecular size (MW 1001 as the bis calcium salt; MW 480 as the free acid) rosuvastatin has difficulty crossing biological membranes. Rosuvastatin is also relatively poorly soluble in water under both acidic and basic conditions. For example, as defined by the U.S. Pharmacopeia (2002), rosuvastatin is considered "sparingly soluble."

As with other statins, rosuvastatin competitively inhibits HMG-CoA reductase and is thus useful in reducing levels of LDL-C, total cholesterol, and triglycerides, as well as increasing high-density-lipoprotein cholesterol (HDL-C) levels. Although rosuvastatin has only recently received final FDA approval, clinical studies suggest that it may be more effective in reducing LDL-C and total cholesterol levels than either pravastatin or simvastatin (Cheng-Lai (2003) *Heart Disease* 5:72). The extra methane sulfonamide group in rosuvastatin is believed to result in an additional ionic binding interaction with, and thus greater affinity for, HMG-CoA reductase. Accordingly, rosuvastatin has the lowest $IC_{50}$ (0.16 nM in rat hepatocytes) and is the most potent inhibitor of sterol synthesis in hepatocytes of all the statins (White (2002) *J. Clin. Pharmacol.* 42:963).

Rosuvastatin reduces LDL-C levels by 34% to 65%, depending on the dosage. Rosuvastatin also increases HDL-C levels by 9% to 14% and reduces triglyceride levels by 10% to 35%. (Igel et al. (2002) *J. Clin. Pharmacol.* 42:835). Furthermore, rosuvastatin is well tolerated in humans at doses ranging from 1 to 40 mg, with Similar adverse side effects to those observed for pravastatin, atorvastatin, and simvastatin, such as rhabdomyolysis. Id. In particular, high doses of rosuvastatin (e.g., 80 mg and higher) have been associated with myopathy in phase III clinical trials. Id.

Rosuvastatin is metabolized slowly in the liver, where metabolism by cytochrome P450 isoenzymes is limited. Although one major N-desmethyl metabolite (formed primarily by CYP2C9 and CYP2C19) has been identified, it is seven-fold less active than the parent compound in inhibiting HMG-CoA reductase. Furthermore, it is believed that 90% of the inhibitory activity of rosuvastatin is due to the parent compound (White (2002) *J. Clin. Pharmacol.* 42:963). Accordingly, since rosuvastatin metabolism is slow and limited, clinically significant metabolically mediated interactions with other drugs are not likely (Cheng-Lai (2003) *Heart Disease* 5:72).

Rosuvastatin is selectively taken up into hepatocytes based on a carrier-mediated mechanism, with up to 90% of the absorbed dose extracted by the liver. (Igel et al. (2002) *J. Clin. Pharmacol.* 42:835). Although the presence of food decreases the rate of absorption, the overall extent of absorption remains constant. Peak plasma concentrations ($C_{max}$), as well as the AUC, show a relatively linear relationship with respect to doses ranging from 5 to 80 mg, with a $t_{max}$ that ranges from 3 to 5 hours. (Igel et al. (2002) *J. Clin. Pharmacol.* 42:835). Furthermore, rosuvastatin has a long elimination half-life ($t_{1/2}$) of 20 hours. Clearance of rosuvastatin occurs mainly through biliary excretion (90%), while 10% is excreted in the urine (Cheng-Lai (2003) *Heart Disease* 5:72).

Unlike pravastatin (but like atorvastatin), rosuvastatin is stable in acidic environments like that found in the stomach. Once rosuvastatin passes out of the stomach, it is believed to enter the circulation via a carrier-mediated transport mechanism in the small intestine. Following absorption, rosuvastatin enters hepatocytes through a carrier-mediated transport mechanism. The organic anion transport polypeptide-C, which is expressed at high levels in hepatocytes, is thought to play a key role in selectively delivering rosuvastatin to the HMG-CoA reductase target enzyme in the liver (White (2002) *J. Clin. Pharmacol.* 42:963). Accordingly, the amount of rosuvastatin that is ultimately absorbed by the liver and available for binding to HMG-CoA reductase depends on the rates of uptake in the intestine and liver.

SUMMARY OF THE INVENTION

The present invention relates to methods of increasing the hepatic bioavailability of acid-stable, carrier-mediated transport statins, comprising administering to a subject a therapeutically effective amount of the acid-stable, carrier-mediated transport statin, or a pharmaceutically acceptable salt thereof, in a pharmaceutical formulation. In certain embodiments, the formulation results in release of the statin in the stomach and releases the statin at a rate that avoids saturating the intestinal and hepatocytic absorption mechanisms. In other embodiments, the formulation results in a delayed release of substantial amounts of the statin until the composition has passed out of the stomach, and then releases the statin at a rate that avoids saturating the intestinal and hepatocytic absorption mechanisms.

In one embodiment of this method, the acid-stable, carrier-mediated transport statin is atorvastatin. In another embodiment, the acid-stable, carrier-mediated transport statin is rosuvastatin. In a further embodiment, the administration achieves a relative systemic bioavailability of the acid-stable, carrier-mediated transport statin, as compared to an equally effective dose of a conventional release formulation, of less than about 90%. In another embodiment, the administration achieves a relative systemic bioavailability of the acid-stable, carrier-mediated transport statin, as compared to an equally effective dose of a conventional release formulation, of less than about 80%.

The present invention also encompasses methods of increasing statin hepatic bioavailability by administering statin formulations that release greater than about 80% of their statin content over a period of from about 1 hour to about 8 hours.

The present invention also relates to methods of treating hypercholesterolemia comprising administering to a subject in need of such treatment, a therapeutically effective amount of an acid-stable, carrier-mediated statin, or a pharmaceutically acceptable salt thereof, in a pharmaceutical formulation, wherein the formulation releases the acid-stable, carrier-mediated transport statin over a period of greater than about 2 hours.

In one embodiment of this method, the acid-stable, carrier-mediated transport statin is atorvastatin. In another embodiment, the acid-stable, carrier-mediated transport statin is rosuvastatin.

The present invention also encompasses methods of treating hypercholesterolemia by administering a statin formulation wherein the formulation exhibits an acid-stable, carrier-mediated transport statin release rate as follows:
  2 hours: less than or equal to about 40%;
  4 hours: between about 20% and about 80%; and
  6 hours: greater than about 70%.

The present invention further encompasses modified-release formulations comprising a therapeutically effective amount of an acid-stable, carrier-mediated transport statin, or a pharmaceutically acceptable salt thereof, which formulation releases the acid-stable, carrier-mediated transport statin at a rate that is about equal to or less than the rate of absorption in the intestine and in the liver.

In one embodiment of these formulations, the acid-stable, carrier-mediated transport statin is atorvastatin. In another embodiment, the acid-stable, carrier-mediated transport statin is rosuvastatin. In a further embodiment, the formulation exhibits an acid-stable, carrier-mediated transport statin release rate as follows:
  2 hours: less than or equal to about 40%;
  4 hours: between about 20% and about 80%; and
  6 hours: greater than about 70%.

The invention also relates to methods of increasing the hepatic bioavailability of large molecular weight, carrier-mediated transport statins, comprising administering to a subject a therapeutically effective amount of the large molecular weight, carrier-mediated transport statin, or a pharmaceutically acceptable salt thereof, in a pharmaceutical formulation, wherein the formulation comprises a membrane permeability enhancer and wherein the formulation releases the large molecular weight, carrier-mediated transport statin at a rate that avoids saturating the intestinal and hepatocytic absorption mechanisms.

In one embodiment of this method the large molecular weight, carrier-mediated transport statin is atorvastatin. In another embodiment, the large molecular weight, carrier-mediated transport statin is rosuvastatin. In a further embodiment, these methods use formulations that release greater than about 80% of their statin content over a period of from about 1 hour to about 8 hours. In a further embodiment, these methods use formulations that achieve a relative systemic bioavailability of the large molecular weight, carrier-mediated transport statin, as compared to an equally effective dose of a conventional release formulation, of less than about 90% or less than about 80%.

The present invention also includes methods of treating hypercholesterolemia comprising administering to a subject in need of such treatment, a therapeutically effective amount of large molecular weight, carrier-mediated transport statins, or a pharmaceutically acceptable salt thereof, in a pharmaceutical formulation, wherein the formulation comprises membrane permeability enhancer and wherein the formulation releases the large molecular weight, carrier-mediated transport statin over a period of greater than about 2 hours.

In one embodiment of this method, the large molecular weight, carrier-mediated transport statin is atorvastatin. In another embodiment, the large molecular weight, carrier-mediated transport statin is rosuvastatin. In a further embodiment, the formulation exhibits a large molecular weight, carrier-mediated transport statin release rate as follows:
  2 hours: less than or equal to about 40%;
  4 hours: between about 20% and about 80%; and
  6 hours: greater than about 70%.

The invention also relates to modified-release formulations comprising a therapeutically effective amount of large molecular weight, carrier-mediated transport statins, or a pharmaceutically acceptable salt thereof, and membrane permeability enhancers, and wherein the formulation releases the large molecular weight, carrier-mediated transport statins at a rate that is about equal to or less than the rate of absorption in the intestine and in the liver.

In one embodiment of these formulations, the large molecular weight, carrier-mediated transport statin is atorvastatin. In another embodiment, the large molecular weight, carrier-mediated transport statin is rosuvastatin. In another embodiment the formulation exhibits a large molecular weight, carrier-mediated transport statin release rate as follows:
- 2 hours: less than or equal to about 40%;
- 4 hours: between about 20% and about 80%; and
- 6 hours: greater than about 70%.

The present invention also includes methods of increasing the hepatic bioavailability of poorly water-soluble, carrier-mediated transport statins, comprising administering to a subject a therapeutically effective amount of the poorly water-soluble, carrier-mediated transport statin, or a pharmaceutically acceptable salt thereof, in a pharmaceutical formulation, wherein a solubility improving method has been applied to the poorly water-soluble, carrier-mediated transport statin and wherein the formulation releases the statin at a rate that avoids saturating the intestinal and hepatic absorption mechanisms.

In one embodiment of this method, the poorly water-soluble, carrier-mediated transport statin is atorvastatin. In another embodiment the poorly water-soluble, carrier-mediated transport statin is rosuvastatin. In another embodiment, the formulation releases greater than about 80% of its statin content over a period of from about 1 hour to about 8 hours. In another embodiment, administration of the formulation achieves a relative systemic bioavailability of the poorly water-soluble, carrier-mediated transport statin, as compared to an equally effective dose of a conventional release formulation, of less than about 90% or less than about 80%.

The present invention also relates to methods of treating hypercholesterolemia comprising administering to a subject in need of such treatment, a therapeutically effective amount of poorly water-soluble, carrier-mediated transport statins, or a pharmaceutically acceptable salt thereof, in a pharmaceutical formulation, wherein a solubility improving method has been applied to the poorly water-soluble, carrier-mediated transport statin and wherein the formulation releases the poorly water-soluble, carrier-mediated transport statin over a period of greater than about 2 hours.

In one embodiment of this method, the poorly water-soluble, carrier-mediated transport statin is atorvastatin. In another embodiment, the poorly water-soluble, carrier-mediated transport statin is rosuvastatin. In a further embodiment, the formulation exhibits a poorly water-soluble, carrier-mediated transport statin release rate as follows:
- 2 hours: less than or equal to about 40%;
- 4 hours: between about 20% and about 80%; and
- 6 hours: greater than about 70%.

The present invention also relates to modified-release formulations comprising a therapeutically effective amount of a poorly water-soluble, carrier-mediated transport statin, or a pharmaceutically acceptable salt thereof, wherein a solubility improving method has been applied to the poorly water-soluble, carrier-mediated transport statin and which formulation releases the poorly water-soluble, carrier-mediated transport statin at a rate that is about equal to or less than the rate of absorption in the intestine and in the liver.

In one embodiment of these formulations, the poorly water-soluble, carrier-mediated transport statin is atorvastatin. In another embodiment the poorly water-soluble, carrier-mediated transport statin is rosuvastatin. In another embodiment the formulation exhibits a poorly water-soluble, carrier-mediated transport statin release rate as follows:
- 2 hours: less than or equal to about 40%;
- 4 hours: between about 20% and about 80%; and
- 6 hours: greater than about 70%.

DETAILED DESCRIPTION OF THE INVENTION

The uptake of certain statins in the intestine and in the liver is governed by carrier-mediated transport mechanisms. As used herein, the phrase "carrier-mediated transport mechanism" refers to any selective biological membrane transport mechanism, and thus requires additional carrier molecules to transport a given molecule across a membrane. Such carrier-mediated transport mechanisms include active-transport mechanisms, which may require the hydrolysis of ATP. As used herein, the phrase "carrier-mediated transport statin" includes a group of compounds belonging to the statin class of drugs that are transported across biological membranes in vivo by a carrier-mediated transport mechanism, and thus whose rates of absorption are generally limited by the rate of the transport mechanism. The phrase "carrier-mediated transport statin" also includes any statin whose rate of absorption to its primary site of action is dependent on the rate of at least one carrier-mediated transport mechanism in crossing a biological membrane. Examples of carrier-mediated transport statins include pravastatin, atorvastatin, and rosuvastatin. The phrase "carrier-mediated transport statin" also includes any pharmaceutically acceptable salts or stereoisomers of a carrier-mediated transport statin.

As used herein, the terms "atorvastatin" and "rosuvastatin" include atorvastatin, rosuvastatin, and any pharmaceutically acceptable salts, or stereoisomers, thereof. As used herein, the term "pharmaceutically acceptable salt" includes salts that are physiologically tolerated by a patient. Such salts are typically prepared from inorganic acids or bases and/or organic acids or bases. Examples of these acids and bases are well known to those of ordinary skill in the art.

Some statins are stable under acidic conditions. As used herein, the phrase "acid-stable statin" refers to a group of compounds that belong to the statin class of drugs, and that do not substantially degrade or undergo conversion to metabolites under acidic conditions. For example, acid-stable statins are those where less than about 25% of the compound is degraded or converted to metabolites in an environment with a pH of less than about 4. For example, in one embodiment, an acid-stable statin can be a statin where about 20% of the compound is degraded in an environment with a pH of less than about 4. In a further embodiment, an acid-stable statin is a statin where about 15% of the compound is degraded in an environment with a pH of less than about 4. In a further embodiment, an acid-stable statin is a statin where about 10% of the compound is degraded in an environment with a pH of less than about 4. An acid-stable statin can also be a statin where about 5% or less of the compound is degraded in an environment with a pH of less than about 4. The phrase "acid-stable statin" also includes any pharmaceutically acceptable salts, or stereoisomers, of an acid-stable statin. Examples of acid-stable statins include simvastatin, lovastatin, fluvastatin, atorvastatin, and rosuvastatin, derivatives thereof, and their pharmaceutically acceptable salts, and their stereoisomers.

Other statins are poorly soluble in water. As used herein, the term "poorly water-soluble statin" refers to a group of compounds that belong to the statin class of drugs that typically have a solubility that is rated as "sparingly soluble", or lower, as that term is defined by the U.S. Pharmacopeia (2002) (p. 8). The U.S. Pharmacopeia defines several such levels of solubility as follows: "sparingly soluble" refers to an aqueous solubility that ranges from about 1/30 to about 1/100 (mg/ml); "slightly soluble" refers to an aqueous solubility that ranges from about 1/100 to about 1/1,000 (mg/ml); "very slightly soluble" refers to an aqueous solubility that ranges from about 1/1,000 to about 1/10,000 (mg/ml); and "practically insoluble, or insoluble" refers to an aqueous solubility that is 1/10,000 (mg/ml) or less. The phrase "poorly water-soluble statin" also includes any pharmaceutically acceptable salts, or stereoisomers, of a poorly water-soluble statin. Poorly water-soluble statins include, for example, simvastatin, lovastatin, atorvastatin and rosuvastatin, derivatives and stereoisomers thereof, and their pharmaceutically acceptable salts.

Due to their large molecular size, other statins are poorly diffusive permeable through lipid membranes. As used herein, the term "large molecular weight statin" refers to any statin with a molecular weight of greater than about 475 Daltons. For example, large molecular weight statins include statins with molecular weights of greater than about 475, greater than about 500, greater than about 600, greater than about 700, greater than about 800, greater than about 900, or greater than about 1000 Daltons. The phrase "large molecular weight statin" also includes any pharmaceutically acceptable salts, and any stereoisomers, of a large molecular weight statin. Examples of large molecular weight statins include atorvastatin and rosuvastatin, derivatives and stereoisomers thereof, and their pharmaceutically acceptable salts.

One of skill in the art will appreciate that the statin characteristics and properties discussed above are not mutually exclusive and that a given statin may have one or more of these properties. For example, as used herein, the term "acid-stable, carrier-mediated transport statin" refers to a statin that has the characteristics of an acid-stable statin (as discussed above) and is also a carrier-mediated transport statin (as discussed above). Similarly, as used herein, the term "poorly water-soluble, carrier-mediated transport statin" refers to statins that have the characteristics of a poorly water-soluble statin (as described above) as well as being a carrier-mediated transport statin. Further, for example, as used herein, the term "large molecular weight, carrier-mediated transport statin" refers to a statin that is a large molecular weight statin (as described above) as well as being a carrier-mediated transport statin. Examples of acid-stable, poorly water-soluble, large molecular weight, carrier-mediated transport statins include atorvastatin and rosuvastatin, as well as their pharmaceutically acceptable salts, and their stereoisomers.

There exists a need in the art for modified-release formulations that release carrier-mediated transport statins that are either acid-stable, poorly water-soluble, and/or have large molecular weights at rates that do not saturate the rate of uptake in the small intestine and subsequently in the liver. Providing carrier-mediated transport statins at such rates maximizes their hepatic-specific absorption and thus concentrates the statins within the liver. The concentration of the carrier-mediated transport statins in the liver subsequently limits their systemic exposure, resulting in improved safety and tolerability profiles. As used herein, the term "hepatic bioavailability" means the amount of drug that is absorbed into the hepatocyte.

As used herein, the phrase "modified-release" formulation or dosage form includes a pharmaceutical preparation that achieves a desired release of the drug from the formulation. For example, a modified-release formulation may extend the influence or effect of a therapeutically effective dose of an active compound in a patient. In addition to maintaining therapeutic levels of the active compound, a modified-release formulation may also be designed to delay the release of the active compound for a specified period.

The methods and formulations of this invention may be used with other drugs that are of therapeutic benefit in lowering lipid levels. These drugs include other HMG CoA reductase inhibitors, such as pravastatin, fluvastatin, simvastatin, or lovastatin; fibrates, such as gemfibrozil; modifiers of cholesterol absorption, such as ezetimibe; bile acid-binding resins, such as colestipol and cholestyramine; and/or other agents, such as fish oils, nicotinic acid, and probucol. The formulations and methods of this invention, when co-administered with other lipid lowering agents, can be used to reduce the limiting side effects that may be observed when conventional release statin formulations are co-administered with other lipid lowering agents.

Carrier-Mediated Transport Statins

One aspect of the present invention relates to compositions comprising a therapeutically effective amount of at least one carrier-mediated transport statin (or a stereisomer thereof, or a pharmaceutically acceptable salt thereof, and methods for their use. As used herein, the phrase "therapeutically effective amount" includes the amount of carrier-mediated transport statin (or stereoisomers thereof, or pharmaceutically acceptable salts thereof, which alone and/or in combination with other drugs, provides a benefit in the prevention, treatment, and/or management of one or more conditions or diseases that are associated with high cholesterol and/or high lipid levels or may otherwise benefit from a decrease in blood lipid levels or cholesterol levels. Such conditions or diseases include, but are not limited to, hypercholesterolemia, hyperlipidemia, myocardial infarction, atherosclerosis, stroke, ischemia, coronary atherosclerosis, coronary death, and/or cardiovascular mortality. The one or more diseases that can be treated, managed, and/or prevented by the formulations and/or methods of the present invention also include cardiovascular diseases that are not secondary to hypercholesterolemia.

In one embodiment, a therapeutically effective amount of a carrier-mediated transport statin is the amount required to inhibit or reduce the activity of hepatic 3-hydroxy-3-methyl-glutaryl-co-enzyme A (HMG-CoA) reductase.

The compositions may be designed to increase and/or optimize the liver-specific absorption of carrier-mediated transport statins from the intestine, thus limiting systemic exposure to carrier-mediated transport statins and reducing at least one unwanted side effect that results from such exposure, e.g., when a conventional release carrier-mediated transport formulation is administered. As used herein, the term "conventional release formulation" means a formulation that, when tested in a USP dissolution bath in pH 6.8 buffer, releases greater than about 80% of its statin content in less than about 1 hour. As used herein, the term "conventional delayed-release formulation" means a formulation that (when tested in a USP dissolution bath in pH 6.8 buffer) subsequent to an exposure to an acidic environment for 2 hours, releases greater than about 70% of its statin content in less than about 1 hour. The reduction of unwanted side effects is achieved by delivering at least one carrier-mediated transport statin to the liver in a manner that provides a cholesterol-lowering effect for the subject receiving the drug, without significantly inhibiting systemic synthesis of ubiquinone. In particular, the release of carrier-mediated transport statins from the compositions of the invention is targeted to the upper small intestine (the primary site of absorption), at a rate designed to avoid saturating the intestinal absorption apparatus.

The inventive compositions may also achieve a slower rate of absorption than conventional release formulations, which improves delivery to the liver, such that the delivery rate is more consistent with the uptake rate into hepatocytes. This can maximize uptake of carrier-mediated transport statins and maximize subsequent extraction by the liver, providing a dose-sparing effect and significantly reducing the amount of carrier-mediated transport statin diverted to the systemic circulation. While not wishing to be bound by any particular theory, compositions of the present invention may avoid the development of myopathy associated with undesirable depletion of ubiquinone in peripheral tissues.

Optimization of hepatic absorption also permits one to use less carrier-mediated transport statin in the compositions of the present invention, relative to the amounts required in conventional forms of these drugs. Due to the more efficient delivery of the carrier-mediated transport statins achieved by the present compositions, it is possible to decrease the amount of carrier-mediated transport statins included in these compositions. For example, in atorvastatin and rosuvastatin compositions, it is possible to decrease the amount of atorvastatin or rosuvastatin included by about 10% to about 90%, or by about 10% to about 80%, or by about 10% to about 70%, or by about 20% to about 70%, or by about 20% to about 60%, or by about 25% to about 50%, relative to a conventional release formulation of the drug. In one embodiment, the amount of atorvastatin in the composition of the present invention may be reduced to about 25%, relative to a dose of LIPITOR®. In another embodiment, the amount of rosuvastatin in the composition of the present invention may be reduced to about 25%, relative to a dose of CRESTOR®.

The modified-release formulations of the present invention also provide advantages in that equivalent, or higher, doses of carrier-mediated transport statins may be used, with better efficacy and/or fewer side effects observed. For example, atorvastatin formulations of the present invention may include, for example, from 100% to 200% of the amount of atorvastatin in conventional release formulations. Even further, for example, rosuvastatin formulations of the present invention may include, for example, from 100% to 200% of the amount of rosuvastatin in conventional release formulations. However, even with these higher doses, formulations of the present invention achieve better efficacy and fewer side effects.

The compositions of the present invention are suitable for treating and/or preventing conditions or diseases that are benefited by decreasing levels of lipids and/or cholesterol in the body. Such conditions include those that are typically treated and/or prevented with conventional carrier-mediated transport statin compositions, such as coronary events in hypercholesterolemic patients who lack clinically evident coronary heart disease, and coronary events in hypercholesterolemic patients who exhibit clinically evident coronary artery disease. The present compositions may also be used as an adjunctive therapy (to dietary restrictions and exercise) to reduce elevated total cholesterol (Total-C), low density lipoprotein-cholesterol (LDL-C), apolipoprotein B (Apo B), and triglyceride (TG) levels, and to increase high density lipoprotein-cholesterol (HDL-C) levels in subjects with primary hypercholesterolemia and mixed dyslipidemia (Fredrickson Type IIa and IIb), elevated serum triglyceride levels (Fredrickson Type IV), and primary dysbetalipoproteinemia (Fredrickson Type III), in patients that do not respond adequately to dietary restrictions. The present compositions and methods may also be used to treat, manage, and/or prevent one or more cardiovascular diseases that are not secondary to hypercholesterolemia.

Acid-Stable Statins

The present invention is also directed to modified-release formulations comprising a therapeutically effective amount of at least one acid-stable, carrier-mediated transport statin, or a pharmaceutically acceptable salt thereof, and methods for their use, where the formulation does not result in a delayed release during passage from the stomach to the intestine. Optionally, the invention also encompasses formulations of such statins where the release of statin is delayed until the drug has passed from the stomach into the intestine. Because the statins used in the compositions are stable under acidic conditions, the compositions do not require a protective coating to avoid conversion of the statin in the stomach to metabolites prior to absorption in the intestine. Although not required, such protective coatings may nevertheless be used if a delayed release is desired. The option of using, or not using, a protective coating is desirable because it allows a greater degree of flexibility in designing modified-release formulations that release the statin at the desired rate. Thus, when administered to a patient, the compositions of the present invention may or may not delay the release of substantial amounts of acid-stable, carrier-mediated transport statins until the composition has passed out of the stomach and into the intestine.

The compositions may be designed to increase and/or optimize the liver-specific absorption of acid-stable, carrier-mediated transport statins from the intestine, thus limiting their systemic exposure and reducing at least one unwanted side effect that results from such exposure, e.g., when a conventional release acid-stable, carrier-mediated transport formulation is administered. The reduction of unwanted side effects is achieved by delivering at least one acid-stable, carrier-mediated transport statin to the liver in a manner that provides a cholesterol-lowering effect for the subject receiving the drug, without significantly inhibiting systemic synthesis of ubiquinone. In particular, the release of acid-stable, carrier-mediated transport statins from the compositions of the invention is targeted to the upper small intestine (the primary site of absorption), at a rate designed to avoid saturating the intestinal absorption apparatus.

The inventive compositions may also achieve a slower rate of absorption than conventional release formulations, which improves delivery to the liver, such that the delivery rate is more consistent with the uptake rate into hepatocytes. This can maximize uptake of acid-stable, carrier-mediated transport statins and maximize subsequent extraction by the liver, providing a dose-sparing effect and significantly reducing the amount of acid-stable, carrier-mediated transport statin diverted to the systemic circulation. While not wishing to be bound by any particular theory, compositions of the present invention may avoid the development of myopathy associated with undesirable depletion of ubiquinone in peripheral tissues.

Optimization of absorption in the liver also permits one to use less acid-stable, carrier-mediated transport statin in the compositions of the present invention, relative to the amounts required in conventional forms of these drugs. Due to the more efficient delivery of the acid-stable, carrier-mediated transport statins achieved by the present compositions, it is possible to decrease the amount of acid-stable, carrier-mediated transport statins included in these compositions. For example, in atorvastatin and rosuvastatin compositions, it is possible to decrease the amount of atorvastatin or rosuvastatin included by about 10% to about 90%, or by about 10% to about 80%, or by about 10% to about 70%, or by about 20% to about 70%, or by about 20% to about 60%, or by about 25% to about 50%, relative to a conventional release formulation of the drug. In one embodiment, the amount of atorvastatin in the composition of the present invention may be reduced by about 25%, relative to a dose of LIPITOR®. In another embodiment, the amount of rosuvastatin in the composition of the present invention may be reduced by about 25%, relative to a dose of CRESTOR®.

The modified-release formulations of the present invention also provide advantages in that equivalent, or higher, doses of acid-stable, carrier-mediated transport statins may be used, with better efficacy and/or fewer side effects observed. For example, atorvastatin formulations of the present invention may include, for example, from 100% to 200% of the amount of atorvastatin in conventional release formulations. Even further, for example, rosuvastatin formulations of the present invention may include, for example, from 100% to 200% of the amount of rosuvastatin in conventional release formulations. However, even with these higher doses, formulations of the present invention achieve better efficacy and fewer side effects.

The compositions of the present invention are suitable for treating and/or preventing conditions or diseases that are benefited by decreasing levels of lipids and/or cholesterol in the body. Such conditions include those that are typically treated and/or prevented with conventional acid-stable, carrier-mediated transport statin compositions, such as coronary events in hypercholesterolemic patients who lack clinically evident coronary heart disease, and coronary events in hypercholesterolemic patients that exhibit clinically evident coronary artery disease. The present compositions may also be used as an adjunctive therapy (to dietary restrictions and exercise) to reduce elevated total cholesterol (Total-C), LDL-C, apolipoprotein B (Apo B), and triglyceride (TG) levels, and to increase HDL-C levels in subjects with primary hypercholesterolemia and mixed dyslipidemia (Fredrickson Type IIa and IIb), elevated serum triglyceride levels (Fredrickson Type IV), and primary dysbetalipoproteinemia (Fredrickson Type III), in patients who do not respond adequately to dietary restrictions. The present compositions and methods may also be used to treat, manage, and/or prevent one or more cardiovascular diseases that are not secondary to hypercholesterolemia.

Poorly Water-Soluble Statins

The invention also encompasses modified-release formulations comprising a therapeutically effective amount of at least one poorly water-soluble, carrier-mediated transport statin, or a pharmaceutically acceptable salt thereof, and methods for their use, where the solubility of the statin has been improved. Increasing the solubility of a poorly-soluble statin can increase the rate of uptake in the lumina of the intestine. This increase in uptake, however, should be designed so that the plasma levels of the absorbed statin do not saturate the subsequent uptake rate in the liver.

Improving the solubility of a poorly water-soluble statin can be achieved using several methods. As used herein, the term "solubility improving method" refers to any method that, when used as part of the formulation, improves the solubility of a poorly water-soluble statin by at least one level of solubility as defined in the U.S. Pharmacopeia (2002). For example, in one embodiment the solubility is improved from "slightly soluble" to "sparingly soluble." In another embodiment, the solubility is improved from "very slightly soluble" to "slightly soluble". In a further embodiment, the solubility is improved from "practically insoluble, or insoluble" to "very slightly soluble."

In one embodiment, the solubility of the poorly water-soluble statin can be improved by micronization. This is accomplished by conventional micronization techniques known to those of skill in the art, for example, jet milling, air jet milling, impact milling, media milling (aqueous or solvent), ball milling, pin milling, or fluid bed milling. In one embodiment of the invention, about 90% of the drug particles are less than about 20 microns in size. In another embodiment, about 50% of the drug particles are not more than about 10 microns in size. In some embodiments, particles of the poorly water-soluble statin are prepared as an even smaller, e.g., sub-micron, size.

Additionally, excipients may be included in the formulation to enhance the solubility/dissolution of the poorly water-soluble drugs. For example, surfactants, detergents, or any other agents that improve the dissolution of the statins may be included in the formulation. Such surfactants include, but are not limited to, sodium lauryl sulphate. The formulations of this invention also contemplate incorporation of suitable excipients to maintain the integrity of particles of the active ingredient.

The compositions may be designed to increase and/or optimize the liver-specific absorption of poorly water-soluble, carrier-mediated transport statins from the intestine, thus limiting their systemic exposure and reducing at least one unwanted side effect that results from such exposure, e.g., when a conventional poorly water-soluble, carrier-mediated transport formulation is administered. The reduction of unwanted side effects is achieved by delivering at least one poorly water-soluble, carrier-mediated transport statin to the liver in a manner that provides a cholesterol-lowering effect for the subject receiving the drug, without significantly inhibiting systemic synthesis of ubiquinone. In particular, the release of poorly water-soluble, carrier-mediated transport statins from the compositions of the invention is targeted to the upper small intestine (the primary site of absorption), at a rate designed to avoid saturating the intestinal absorption apparatus.

The inventive compositions may also achieve a slower rate of absorption than conventional release formulations, which improves delivery to the liver, such that the delivery rate is more consistent with the uptake rate into hepatocytes. This can maximize uptake of poorly water-soluble, carrier-mediated transport statins and maximize subsequent extraction by the liver, providing a dose-sparing effect and significantly reducing the amount of poorly water-soluble, carrier-mediated transport statin diverted to the systemic circulation. While not wishing to be bound by any particular theory, compositions of the present invention may avoid the development of myopathy associated with undesirable depletion of ubiquinone in peripheral tissues.

Optimization of absorption in the liver also permits one to use less poorly water-soluble, carrier-mediated transport statin in the compositions of the present invention, relative to the amounts required in conventional forms of these drugs. Due to the more efficient delivery of the poorly water-soluble, carrier-mediated transport statins achieved by the present compositions, it is possible to decrease the amount of poorly water-soluble, carrier-mediated transport statins included in these compositions. For example, in atorvastatin and rosuvastatin compositions, it is possible to decrease the amount of atorvastatin or rosuvastatin included by about 10% to about 90%, or by about 10% to about 80%, or by about 10% to about 70%, or by about 20% to about 70%, or by about 20% to about 60%, or by about 25% to about 50%, relative to a conventional release formulation of the drug. In one embodiment, the amount of atorvastatin in the composition of the present invention may be reduced by about 25%, relative to a dose of LIPITOR®. In another embodiment, the amount of rosuvastatin in the composition of the present invention may be reduced by about 25%, relative to a dose of CRESTOR®.

The modified-release formulations of the present invention also provide advantages in that equivalent, or higher, doses of poorly water-soluble, carrier-mediated transport statins may be used, with better efficacy and/or fewer side effects observed. For example, atorvastatin formulations of the present invention may include, for example, from 100% to 200% of the amount of atorvastatin in conventional release formulations. Even further, for example, rosuvastatin formulations of the present invention may include, for example, from 100% to 200% of the amount of rosuvastatin in conventional release formulations. However, even with these higher doses, formulations of the present invention achieve better efficacy and fewer side effects.

The compositions of the present invention are suitable for treating and/or preventing conditions or diseases that are benefited by decreasing levels of lipids and/or cholesterol in the body. Such conditions include those that are typically treated and/or prevented with conventional poorly water-soluble, carrier-mediated transport statin compositions, such as coronary events in hypercholesterolemic patients who lack clinically evident coronary heart disease, and coronary events in hypercholesterolemic patients that exhibit clinically evident coronary artery disease. The present compositions may also be used as an adjunctive therapy (to dietary restrictions and exercise) to reduce elevated total cholesterol (Total-C), LDL-C, apolipoprotein B (Apo B), and triglyceride (TG) levels, and to increase HDL-C levels in subjects with primary hypercholesterolemia and mixed dyslipidemia (Fredrickson Type IIa and IIb), elevated serum triglyceride levels (Fredrickson Type IV), and primary dysbetalipoproteinemia (Fredrickson Type III), in patients who do not respond adequately to dietary restrictions. The present compositions and methods may also be used to treat, manage, and/or prevent one or more cardiovascular diseases that are not secondary to hypercholesterolemia.

Large Molecular Weight Statins

The present invention also relates to modified-release formulations that comprise a therapeutically effective amount of at least one large molecular weight, carrier-mediated transport statin, or a pharmaceutically acceptable salt thereof, and methods for their use, where the membrane permeability of the large molecular weight statin is improved by the addition of an enhancing agent. Such formulations where the permeability of the large molecular weight statin is improved can increase its overall bioavailability. As used herein, the term "membrane permeability enhancer" refers to any agent that improves the membrane permeability of a large molecular weight statin. Various approaches can be used to achieve an enhancement of intestinal permeability to statins that have poor permeability characteristics due to their large molecular size. For example, permeation enhancer agents can be successfully used to produce a transient and reversible alteration in gastrointestinal permeability. This approach can be used for enhancing the intestinal absorption of large molecular weight statins. Although intestinal uptake can be increased in this manner, intestinal uptake rates that subsequently saturate the uptake rate in the liver should be avoided in order to minimize the systemic bioavailability of the statin.

Enhancing agents that can be used to increase intestinal uptake include, but are not limited to, medium chain fatty acids, such as six-carbon to twenty-carbon fatty acids, and in particular the eight- and ten-carbon forms, such as sodium caprate. Such agents include, but are not limited to, fatty acids, fatty acid esters, and fatty alcohols. Such compounds may be hydrophobic or have limited water solubility, and the compounds may have a molecular weight of from about 150 to about 300 Daltons. Fatty alcohols include, but are not limited to, stearyl alcohol, and oleyl alcohol. Fatty acids include, but are not limited to, oleic acid, lauric acid, myristic acid, palmitic acid, stearic acid, linoleic acid, capric acid, monoglycerides, diglycerides, acylcholines, caprylic acids, acylcarnitines, sodium caprate, and palmitoleic acid. Fatty acid esters containing more than 10 to 12 carbons can also be used. Examples of fatty acid esters include, but are not limited to, isopropyl myristate and methyl and ethyl esters of oleic and lauric acid.

Ionic enhancers can also be used. Examples of ionic enhancers that can be used include, but are not limited to, sodium lauryl sulfate, sodium laurate, polyoxyethylene 20-cetylether, laureth-9, sodium dodecylsulfate, and dioctyl sodium sulfosuccinate.

Bile salts can also be used. Examples of bile salts that can be used include, but are not limited to, sodium glycocholate, sodium deoxycholate, sodium taurocholate, sodium taurodihydrofusidate, and sodium glycodihydrofusidate.

Chelating agents can be used. Examples of chelating agents that can be used include, but are not limited to, ethylenediamine tetra-acetic acid (EDTA), citric acid, and salicylates.

Another group of enhancers includes low molecular weight alcohols. Such alcohols can have a molecular weight of less than about 200 Daltons, or less than about 150 Daltons, or less than about 100 Daltons. They can also be hydrophilic, having greater than about 2 wt %, about 5 wt %, or about 10 wt % solubility in water at room temperature. Examples of such alcohols include, but are not limited to, methanol, ethanol, propanol, isopropanol, butanol, benzyl alcohol, glycerin, polyethylene glycol, propanediol, and propylene glycol.

Sulfoxides can also be used. Examples of sulfoxides include, but are not limited to, dimethyl sulfoxide and decmethyl sulfoxide.

Other enhancers that can be used include urea and its derivatives, unsaturated cyclic ureas, 1-dodecylazacycloheptan-2-one, cyclodextrin, enamine derivatives, terpenes, liposomes, acyl carnitines, cholines, peptides (including polyarginine sequences or arginine rich sequences), peptidomimetics, diethyl hexyl phthalate, octyldodecyl myristate, isostearyl isostearate, caprylic/capric triglyceride, glyceryl oleate, and various oils (such as wintergreen or eucalyptol).

Other examples of enhancers suitable for use in the present invention are provided by Santus et al. (1993) Journal of Controlled Release 25:1, and *Remington*, both of which are incorporated by reference herein for their discussion of enhancers.

The compositions may be designed to increase and/or optimize the liver-specific absorption of large molecular weight, carrier-mediated transport statins from the intestine, thus limiting their systemic exposure and reducing at least one unwanted side effect that results from such exposure, e.g., when a conventional large molecular weight, carrier-mediated transport statin formulation is administered. The reduction of unwanted side effects is achieved by delivering at least one large molecular weight, carrier-mediated transport statin to the liver in a manner that provides a cholesterol-lowering effect for the subject receiving the drug, without significantly inhibiting systemic synthesis of ubiquinone. In particular, the release of large molecular weight, carrier-mediated transport statins from the compositions of the invention is targeted to the upper small intestine (the primary site of absorption), at a rate designed to avoid saturating the intestinal absorption apparatus.

The inventive compositions may also achieve a slower rate of absorption than conventional release formulations, which improves delivery to the liver, such that the delivery rate is more consistent with the uptake rate into hepatocytes. This can maximize uptake of large molecular weight, carrier-mediated transport statins and maximize subsequent extraction by the liver, providing a dose-sparing effect and significantly reducing the amount of large molecular weight, carrier-mediated transport statin diverted to the systemic circulation. While not wishing to be bound by any particular theory, compositions of the present invention may avoid the development of myopathy associated with undesirable depletion of ubiquinone in peripheral tissues.

Optimization of absorption in the liver also permits one to use less large molecular weight, carrier-mediated transport statin in the compositions of the present invention, relative to the amounts required in conventional forms of these drugs. Due to the more efficient delivery of the large molecular weight, carrier-mediated transport statins achieved by the present compositions, it is possible to decrease the amount of large molecular weight, carrier-mediated transport statins included in these compositions. For example, in atorvastatin and rosuvastatin compositions, it is possible to decrease the amount of atorvastatin or rosuvastatin included by about 10% to about 90%, or by about 10% to about 80%, or by about 10% to about 70%, or by about 20% to about 70%, or by about 20% to about 60%, or by about 25% to about 50%, relative to a conventional release formulation of the drug. In one embodiment, the amount of atorvastatin in the composition of the present invention may be reduced by about 25%, relative to a dose of LIPITOR®. In another embodiment, the amount of rosuvastatin in the composition of the present invention may be reduced by about 25%, relative to a dose of CRESTOR®.

The modified-release formulations of the present invention also provide advantages in that equivalent, or higher, doses of large molecular weight, carrier-mediated transport statins may be used, with better efficacy and/or fewer side effects observed. For example, atorvastatin formulations of the present invention may include, for example, from 100% to 200% of the amount of atorvastatin in conventional release formulations. Even further, for example, rosuvastatin formulations of the present invention may include, for example, from 100% to 200% of the amount of rosuvastatin in conventional release formulations. However, even with these higher doses, formulations of the present invention achieve better efficacy and fewer side effects.

The compositions of the present invention are suitable for treating and/or preventing conditions or diseases that are benefited by decreasing levels of lipids and/or cholesterol in the body. Such conditions include those that are typically treated and/or prevented with conventional large molecular weight, carrier-mediated transport statin compositions, such as coronary events in hypercholesterolemic patients who lack clinically evident coronary heart disease, and coronary events in hypercholesterolemic patients that exhibit clinically evident coronary artery disease. The present compositions may also be used as an adjunctive therapy (to dietary restrictions and exercise) to reduce elevated total cholesterol (Total-C), LDL-C, apolipoprotein B (Apo B), and triglyceride (TG) levels, and to increase HDL-C levels in subjects with primary hypercholesterolemia and mixed dyslipidemia (Fredrickson Type IIa and IIb), elevated serum triglyceride levels (Fredrickson Type IV), and primary dysbetalipoproteinemia (Fredrickson Type III), in patients who do not respond adequately to dietary restrictions. The present compositions and methods may also be used to treat, manage, and/or prevent one or more cardiovascular diseases that are not secondary to hypercholesterolemia.

The compositions of the present invention may be formulated into a dosage form that modifies the release of carrier-mediated transport statins. Examples of suitable modified-release formulations that may be used in accordance with the present invention include, but are not limited to, matrix systems, osmotic pumps, and membrane controlled dosage forms. These formulations may be single-unit or multi-unit compositions. The formulations of the present invention may comprise at least one carrier-mediated transport statin, that may also be either acid-stable, poorly water-soluble, and/or have a large molecular weight, such as, for example, atorvastatin and rosuvastatin, derivatives or stereoisomers thereof, or pharmaceutically acceptable salts thereof. Each of these types of dosage forms are briefly described below. A more detailed discussion of such forms may also be found in, for example *The Handbook of Pharmaceutical Controlled Release Technology*, D. L. Wise (ed.), Marcel Dekker, Inc., New York (2000); and also in *Treatise on Controlled Drug Delivery: Fundamentals, Optimization, and Applications*, A. Kydonieus (ed.), Marcel Dekker, Inc., New York, (1992), the relevant contents of each of which is hereby incorporated by reference for this purpose.

Matrix-Based Dosage Forms

In some embodiments, the modified-release formulations of the present invention are provided as matrix-based dosage forms. Matrix formulations according to the invention may include hydrophilic, e.g., water-soluble, and/or hydrophobic, e.g., water-insoluble, polymers. The matrix formulations of the present invention may optionally be prepared with functional coatings, which may be enteric, e.g., exhibiting a pH-dependent solubility, or non-enteric, e.g., exhibiting a pH-independent solubility.

Matrix formulations of the present invention may be prepared by using, for example, direct compression or wet granulation. A functional coating, as noted above, may then be applied in accordance with the invention. Additionally, a barrier or sealant coat may be applied over a matrix tablet core prior to application of a functional coating. The barrier or sealant coat may serve the purpose of separating an active ingredient from a functional coating, which may interact with the active ingredient, or it may prevent moisture from contacting the active ingredient. Details of barriers and sealants are provided below.

In a matrix-based dosage form in accordance with the present invention, the carrier-mediated transport statin and optional pharmaceutically acceptable excipient(s) are dispersed within a polymeric matrix, which typically comprises one or more water-soluble polymers and/or one or more water-insoluble polymers. The drug may be released from the dosage form by diffusion and/or erosion. Such matrix systems are described in detail by Wise and Kydonieus, supra.

Suitable water-soluble polymers include, but are not limited to, polyvinyl alcohol, polyvinylpyrrolidone, methylcellulose, hydroxypropylcellulose, hydroxypropylmethyl cellulose, or polyethylene glycol, and/or mixtures thereof.

Suitable water-insoluble polymers include, but are not limited to, ethylcellulose, cellulose acetate, cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride), or polyurethane, and/or mixtures thereof.

As used herein, the term "pharmaceutically acceptable excipients" includes ingredients that are compatible with the other ingredients in a pharmaceutical formulation, in particular the active ingredients, and not injurious to the patient when administered in acceptable amounts. Suitable pharmaceutically acceptable excipients include, but are not limited to, carriers, such as sodium citrate and dicalcium phosphate; fillers or extenders, such as stearates, silicas, gypsum, starches, lactose, sucrose, glucose, mannitol, talc, and silicic acid; binders, such as hydroxypropyl methylcellulose, hydroxymethyl-cellulose, alginates, gelatin, polyvinyl pyrrolidone, sucrose, and acacia; humectants, such as glycerol; disintegrating agents, such as agar, calcium carbonate, potato and tapioca starch, alginic acid, certain silicates, EXPLOTAB™, crospovidone, and sodium carbonate; solution retarding agents, such as paraffin; absorption accelerators, such as quaternary ammonium compounds; wetting agents, such as cetyl alcohol and glycerol monostearate; absorbents, such as kaolin and bentonite clay; lubricants, such as talc, calcium stearate, magnesium stearate, solid polyethylene glycols, and sodium lauryl sulfate; stabilizers, such as fumaric acid; coloring agents; buffering agents; dispersing agents; preservatives; organic acids; and organic bases. The aforementioned excipients are given as examples only and are not meant to include all possible choices. Additionally, many excipients may have more than one role or function, or be classified in more than one group. Such classifications are descriptive only, and not intended to limit any use of a particular excipient.

In one embodiment, a matrix-based dosage form comprises atorvastatin; at least one diluent such as lactose or microcrystalline cellulose (AVICEL™); at least one controlled-release polymer such as METHOCEL™ or polyvinyl pyrrolidone; a permeability enhancer such as sodium caprate; a glidant such as colloidal silicon dioxide; a lubricant such as magnesium state; and a surfactant, such as sodium lauryl sulfate. This composition is compressed into a polymeric matrix that comprises at least one water soluble polymer such as hydroxypropylmethyl cellulose.

The amounts and types of polymers, and the ratio of water-soluble polymers to water-insoluble polymers in the inventive formulations are generally selected to achieve a desired release profile of at least one carrier-mediated transport statin, as described below. For example, by increasing the amount of water insoluble-polymer relative to the amount of water soluble-polymer, the release of the drug may be delayed or slowed. This is due, in part, to an increased impermeability of the polymeric matrix, and, in some cases, to a decreased rate of erosion during transit through the GI tract.

Osmotic Pump Dosage Forms

In another embodiment, the modified-release formulations of the present invention are provided as osmotic pump dosage forms. In an osmotic pump dosage form, a core containing the carrier-mediated transport statin and optionally one or more osmotic excipients is typically encased by a selectively permeable membrane having at least one orifice. The selectively permeable membrane is generally permeable to water, but impermeable to the drug. When the system is exposed to body fluids, water penetrates through the selectively permeable membrane into the core containing the drug and optional osmotic excipients. The osmotic pressure increases within the dosage form. Consequently, the drug is released through the orifice(s) in an attempt to equalize the osmotic pressure across the selectively permeable membrane.

In more complex pumps, the dosage form may contain two internal compartments in the core. The first compartment contains the drug and the second compartment may contain a polymer, which swells on contact with aqueous fluid. After ingestion, this polymer swells into the drug-containing compartment, diminishing the volume occupied by the drug, thereby delivering the drug from the device at a controlled rate over an extended period of time. Such dosage forms are often used when a zero order release profile is desired.

Osmotic pumps are well known in the art. For example, U.S. Pat. Nos. 4,088,864, 4,200,098, and 5,573,776, each of which is hereby incorporated by reference for this purpose, describe osmotic pumps and methods of their manufacture. The osmotic pumps useful in accordance with the present invention may be formed by compressing a tablet of an osmotically active drug, or an osmotically inactive drug in combination with an osmotically active agent, and then coating the tablet with a selectively permeable membrane which is permeable to an exterior aqueous-based fluid but impermeable to the drug and/or osmotic agent.

One or more delivery orifices may be drilled through the selectively permeable membrane wall. Alternatively, one or more orifices in the wall may be formed by incorporating leachable pore-forming materials in the wall. In operation, the exterior aqueous-based fluid is imbibed through the selectively permeable membrane wall and contacts the drug to form a solution or suspension of the drug. The drug solution or suspension is then pumped out through the orifice as fresh fluid is imbibed through the selectively permeable membrane.

Typical materials for the selectively permeable membrane include selectively permeable polymers known in the art to be useful in osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethyl aminoacetate, cellulose acetate ethyl carbamate, cellulose acetate chloracetate, cellulose dipalmitate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, lightly cross-linked polystyrene derivatives, cross-linked poly(sodium styrene sulfonate), poly(vinylbenzyltrimethyl ammonium chloride), and/or mixtures thereof.

The osmotic agents that can be used in the pump are typically soluble in the fluid that enters the device following administration, resulting in an osmotic pressure gradient across the selectively permeable wall against the exterior fluid. Suitable osmotic agents include, but are not limited to, magnesium sulfate, calcium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol, inositol, raffinose, sucrose, glucose, hydrophilic polymers such as cellulose polymers, and/or mixtures thereof.

As discussed above, the osmotic pump dosage form may contain a second compartment containing a swellable polymer. Suitable swellable polymers typically interact with water and/or aqueous biological fluids, which causes them to swell or expand to an equilibrium state. Acceptable polymers exhibit the ability to swell in water and/or aqueous biological fluids, retaining a significant portion of such imbibed fluids within their polymeric structure, so as to increase the hydrostatic pressure within the dosage form. The polymers may swell or expand to a very high degree, usually exhibiting a 2- to 50-fold volume increase. The polymers can be non-cross-linked or cross-linked. In one embodiment, the swellable polymers are hydrophilic polymers. Suitable polymers include, but are not limited to, poly(hydroxy alkyl methacrylate) having a molecular weight of from about 30,000 to about 5,000,000; kappa-carrageenan; polyvinylpyrrolidone having a molecular weight of from about 10,000 to about 360,000; anionic and cationic hydrogels; polyelectrolyte complexes; poly(vinyl alcohol) having low amounts of acetate, cross-linked with glyoxal, formaldehyde, or glutaraldehyde, and having a degree of polymerization from about 200 to about 30,000; a mixture including methyl cellulose, cross-linked agar and carboxymethyl cellulose; a water-insoluble, water-swellable copolymer produced by forming a dispersion of finely divided maleic anhydride with styrene, ethylene, propylene, butylene, or isobutylene; water-swellable polymers of N-vinyl lactams; and/or mixtures of any of the foregoing.

The term "orifice" as used herein comprises means and methods suitable for releasing the drug from the dosage form. The expression includes one or more apertures or orifices that have been bored through the selectively permeable membrane by mechanical procedures. Alternatively, an orifice may be formed by incorporating an erodible element, such as a gelatin plug, in the selectively permeable membrane. In such cases, the pores of the selectively permeable membrane form a "passageway" for the passage of the drug. Such "passageway" formulations are described, for example, in U.S. Pat. Nos. 3,845,770 and 3,916,899, the relevant disclosures of which are incorporated herein by reference for this purpose.

The osmotic pumps useful in accordance with this invention may be manufactured by techniques known in the art. For example, the drug and other ingredients may be milled together and pressed into a solid having the desired dimensions (e.g., corresponding to the first compartment). The swellable polymer is then formed, placed in contact with the drug, and both are surrounded with the selectively permeable agent. If desired, the drug component and polymer component may be pressed together before applying the selectively permeable membrane. The selectively permeable membrane may be applied by any suitable method, for example, by molding, spraying, or dipping.

Membrane-Controlled Dosage Forms

The modified-release formulations of the present invention may also be provided as membrane-controlled formulations. Membrane-controlled formulations of the present invention can be made by preparing a rapid release core, which may be a monolithic (e.g., tablet) or multi-unit (e.g., pellet) type, and coating the core with a membrane. The membrane-controlled core can then be further coated with a functional coating. In between the membrane-controlled core and the functional coating, a barrier or sealant may be applied. The barrier or sealant may alternatively, or additionally, be provided between the rapid release core and the membrane coating. Details of membrane-controlled dosage forms are provided below.

In one embodiment, carrier-mediated transport statins are provided in multiparticulate membrane-controlled formulations. The carrier-mediated transport statins may be formed into an active core by applying the drug to a nonpareil seed having an average diameter in the range of about 0.4 to about 1.1 mm or about 0.85 to about 1.00 mm. The carrier-mediated transport statin may be applied with or without additional excipients onto the inert cores, and may be sprayed from solution or suspension using a fluidized bed coater (e.g., Wurster coating) or pan coating system. Alternatively, carrier-mediated transport statins may be applied as a powder onto the inert cores using a binder to bind the carrier-mediated transport statins onto the cores. Active cores may also be formed by extrusion of the core with suitable plasticizers (described below) and any other processing aids as necessary.

The modified-release formulations of the present invention comprise at least one polymeric material, which is applied as a membrane coating to the drug-containing cores. Suitable water-soluble polymers include, but are not limited to, polyvinyl alcohol, polyvinylpyrrolidone, methylcellulose, hydroxypropylcellulose, hydroxypropylmethyl cellulose or polyethylene glycol, and/or mixtures thereof.

Suitable water-insoluble polymers include, but are not limited to, ethylcellulose, cellulose acetate, cellulose propionate, cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), poly (ethylene), poly (ethylene) low density, poly (ethylene) high density, poly (ethylene oxide), poly (ethylene terephthalate), poly (vinyl isobutyl ether), poly (vinyl acetate), poly (vinyl chloride), or polyurethane, and/or mixtures thereof.

EUDRAGIT™ polymers (available from Rohm Pharma) are polymeric lacquer substances based on acrylates and/or methacrylates. A suitable polymer that is freely permeable to the active ingredient and water is EUDRAGIT™ RL. A suitable polymer that is slightly permeable to the active ingredient and water is EUDRAGIT™ RS. Other suitable polymers which are slightly permeable to the active ingredient and water, and exhibit a pH-dependent permeability include, but are not limited to, EUDRAGIT™ L, EUDRAGIT™ S, and EUDRAGIT™ E.

EUDRAGIT™ RL and RS are acrylic resins comprising copolymers of acrylic and methacrylic acid esters with a low content of quaternary ammonium groups. The ammonium groups are present as salts and give rise to the permeability of the lacquer films. EUDRAGIT™ RL and RS are freely permeable (RL) and slightly permeable (RS), respectively, independent of pH. The polymers swell in water and digestive juices, in a pH-independent manner. In the swollen state, they are permeable to water and to dissolved active compounds.

EUDRAGIT™ L is an anionic polymer synthesized from methacrylic acid and methacrylic acid methyl ester. It is insoluble in acids and pure water. It becomes soluble in neutral to weakly alkaline conditions. The permeability of EUDRAGIT™ L is pH dependent. Above pH 5.0, the polymer becomes increasingly permeable.

In one embodiment comprising a membrane-controlled dosage form, the polymeric material comprises methacrylic acid co-polymers, ammonio methacrylate co-polymers, or a mixture thereof. Methacrylic acid co-polymers such as EUDRAGIT™ S and EUDRAGIT™ L (Rohm Pharma) are particularly suitable for use in the controlled-release formulations of the present invention. These polymers are gastroresistant and enterosoluble polymers. Their polymer films are insoluble in pure water and diluted acids. They dissolve at higher pHs, depending on their content of carboxylic acid. EUDRAGIT™ S and EUDRAGIT™ L can be used as single components in the polymer coating or in combination in any ratio. By using a combination of the polymers, the polymeric material may exhibit a solubility at a pH between the pHs at which EUDRAGIT™ L and EUDRAGIT™ S are separately soluble.

The membrane coating may comprise a polymeric material comprising a major proportion (i.e., greater than 50% of the total polymeric content) of one or more pharmaceutically acceptable water-soluble polymers, and optionally a minor proportion (i.e., less than 50% of the total polymeric content)

of one or more pharmaceutically acceptable water-insoluble polymers. Alternatively, the membrane coating may comprise a polymeric material comprising a major proportion (i.e., greater than 50% of the total polymeric content) of one or more pharmaceutically acceptable water-insoluble polymers, and optionally a minor proportion (i.e., less than 50% of the total polymeric content) of one or more pharmaceutically acceptable water-soluble polymers.

Ammonio methacrylate co-polymers such as EUDRAGIT™ RS and EUDRAGIT™ RL (Rohm Pharma) are suitable for use in the controlled-release formulations of the present invention. These polymers are insoluble in pure water, dilute acids, buffer solutions, or digestive fluids over the entire physiological pH range. The polymers swell in water and digestive fluids independently of pH. In the swollen state they are then permeable to water and dissolved therapeutic agents. The permeability of the polymers depends on the ratio of ethylacrylate (EA), methyl methacrylate (MMA), and trimethylammonioethyl methacrylate chloride (TAMCI) groups in the polymer. Those polymers having EA:MMA: TAMCI ratios of 1:2:0.2 (EUDRAGIT™ RL) are more permeable than those with ratios of 1:2:0.1 (EUDRAGIT™ RS). Polymers of EUDRAGIT™ RL are insoluble polymers of high permeability. Polymers of EUDRAGIT™ RS are insoluble films of low permeability.

The ammonio methacrylate co-polymers may be combined in any desired ratio. For example, a ratio of EUDRAGIT™ RS:EUDRAGIT™ RL (90:10) may be used. The ratios may furthermore be adjusted to provide a delay in release of the drug. For example, the ratio of EUDRAGIT™ RS:EUDRAGIT™ RL may be about 100:0 to about 80:20, about 100:0 to about 90:10, or any ratio in between. In such formulations, the less permeable polymer EUDRAGIT™ RS would generally comprise the majority of the polymeric material.

The ammonio methacrylate co-polymers may be combined with the methacrylic acid co-polymers within the polymeric material in order to achieve the desired delay in the release of the drug. Ratios of ammonio methacrylate co-polymer (e.g., EUDRAGIT™ RS) to methacrylic acid co-polymer in the range of about 99:1 to about 20:80 may be used. The two types of polymers can also be combined into the same polymeric material, or provided as separate coats that are applied to the core.

In addition to the EUDRAGIT™ polymers described above, a number of other such copolymers may be used to control drug release. These include methacrylate ester co-polymers (e.g., EUDRAGIT™ NE 30D). Further information on the EUDRAGIT™ polymers can be found in "Chemistry and Application Properties of Polymethacrylate Coating Systems," in *Aqueous Polymeric Coatings for Pharmaceutical Dosage Forms*, ed. James McGinity, Marcel Dekker Inc., New York, (pp. 109-114).

In addition to the EUDRAGIT™ polymers discussed above, other enteric, or pH-dependent, polymers may be used. Such polymers may include phthalate, butyrate, succinate, and/or mellitate groups. Such polymers include, but are not limited to, cellulose acetate phthalate, cellulose acetate succinate, cellulose hydrogen phthalate, cellulose acetate trimellitate, hydroxypropyl-methylcellulose phthalate, hydroxypropylmethylcellulose acetate succinate, starch acetate phthalate, amylose acetate phthalate, polyvinyl acetate phthalate, and polyvinyl butyrate phthalate.

The coating membrane may further comprise one or more soluble excipients so as to increase the permeability of the polymeric material. Suitably, the soluble excipient is selected from among a soluble polymer, a surfactant, an alkali metal salt, an organic acid, a sugar, and a sugar alcohol. Such soluble excipients include, but are not limited to, polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose, and sucrose, sugar alcohols such as lactitol, maltitol, mannitol, sorbitol, and xylitol, xanthan gum, dextrins, and maltodextrins. In some embodiments, polyvinyl pyrrolidone, mannitol, and/or polyethylene glycol can be used as soluble excipients. The soluble excipient(s) may be used in an amount of from about 1% to about 10% by weight, based on the total dry weight of the polymer.

In another embodiment, the polymeric material comprises one or more water-insoluble polymers, which are also insoluble in gastrointestinal fluids, and one or more water-soluble pore-forming compounds. For example, the water-insoluble polymer may comprise a terpolymer of polyvinylchloride, polyvinylacetate, and/or polyvinylalcohol. Suitable water-soluble pore-forming compounds include, but are not limited to, saccharose, sodium chloride, potassium chloride, polyvinylpyrrolidone, and/or polyethyleneglycol. The pore-forming compounds may be uniformly or randomly distributed throughout the water insoluble polymer. Typically, the pore-forming compounds comprise about 1 part to about 35 parts for each about 1 to about 10 parts of the water-insoluble polymers.

When such dosage forms come in to contact with the dissolution media (e.g., intestinal fluids), the pore-forming compounds within the polymeric material dissolve to produce a porous structure through which the drug diffuses. Such formulations are described in more detail in U.S. Pat. No. 4,557,925, which relevant part is incorporated herein by reference for this purpose. The porous membrane may also be coated with an enteric coating, as described herein, to inhibit release in the stomach.

In one embodiment, a diffusion-controlled-release dosage form comprises rosuvastatin; at least one diluent, such as lactose anhydrous or microcrystalline cellulose (AVICEL™); at least one lubricant, such as magnesium stearate; a rate controlling membrane comprised of at least one water-insoluble polymer, such as polyvinyl acetate and at least one water soluble polymer such as sucrose.

The polymeric material may also include one or more auxiliary agents such as fillers, plasticizers, and/or anti-foaming agents. Representative fillers include talc, fumed silica, glyceryl monostearate, magnesium stearate, calcium stearate, kaolin, colloidal silica, gypsum, micronized silica, and magnesium trisilicate. The quantity of filler used typically ranges from about 2% to about 300% by weight, and can range from about 20% to about 100%, based on the total dry weight of the polymer. In one embodiment, talc is the filler.

The coating membranes, and functional coatings as well, can also include a material that improves the processing of the polymers. Such materials are generally referred to as plasticizers and include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-1-octyl phthalate, di-1-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. In one embodiment, the plasticizer is dibutyl sebacate. The amount of plasticizer used in the polymeric material typically ranges from about 10% to about 50%, for example, about 10, 20, 30, 40, or 50%, based on the weight of the dry polymer.

Anti-foaming agents can also be included. In one embodiment, the anti-foaming agent is simethicone. The amount of anti-foaming agent used typically comprises from about 0% to about 0.5% of the final formulation.

The amount of polymer to be used in the membrane-controlled formulations is typically adjusted to achieve the desired drug delivery properties, including the amount of drug to be delivered, the rate and location of drug delivery, the time delay of drug release, and the size of the multiparticulates in the formulation. The amount of polymer applied typically provides an about 10% to about 100% weight gain to the cores. In one embodiment, the weight gain from the polymeric material ranges from about 25% to about 70%.

A polymeric membrane may include components in addition to polymers, such as, for example, fillers, plasticizers, stabilizers, or other excipients and processing aids. One example of an additional component of the membrane is sodium hydrogen carbonate, which may act as a stabilizer.

The combination of all solid components of the polymeric material, including co-polymers, fillers, plasticizers, and optional excipients and processing aids, typically provides an about 10% to about 450% weight gain on the cores. In one embodiment, the weight gain is about 30% to about 160%.

The polymeric material can be applied by any known method, for example, by spraying using a fluidized bed coater (e.g., Wurster coating) or pan coating system. Coated cores are typically dried or cured after application of the polymeric material. Curing means that the multiparticulates are held at a controlled temperature for a time sufficient to provide stable release rates. Curing can be performed, for example, in an oven or in a fluid bed drier. Curing can be carried out at a temperature above the glass transition temperature of the polymeric material used in the formulation, for example at about 30° C., 40° C., 50° C., or 60° C., depending on the polymer.

A sealant or barrier can also be applied to the polymeric coating. Alternatively, or additionally, a sealant or barrier layer may be applied to the core prior to applying the polymeric material. A sealant or barrier layer is generally not intended to modify the release of carrier-mediated transport statins. Suitable sealants or barriers are permeable or soluble agents such as hydroxypropyl methylcellulose, hydroxypropyl cellulose, hydroxypropyl ethylcellulose, polyvinyl pyrrolidone, and xanthan gum. An outer sealant/barrier, for example, might be used to improve moisture resistance of the entire formulation. A sealant/barrier between the core and the coating, for example, might be used to protect the core contents from an outer polymeric coating that may exhibit pH-dependent or pH-independent dissolution properties. Additionally, there may be instances in which both effects are desired, i.e., moisture resistance and core protection, in which a sealant/barrier is applied between the core and the polymeric membrane coating, and then outside the polymeric membrane coating.

Other agents can be added to improve the processability of a sealant or barrier layer. Such agents include talc, colloidal silica, polyvinyl alcohol, titanium dioxide, micronized silica, fumed silica, glycerol monostearate, magnesium trisilicate, and magnesium stearate, or a mixture thereof. The sealant or barrier layer can be applied from solution (e.g., aqueous) or suspension using any known means, such as a fluidized bed coater (e.g., Wurster coating) or pan coating system. Suitable sealants or barriers include, for example, OPADRY WHITE Y-1-7000 and OPADRY OY/B/28920 WHITE, each of which is available from Colorcon Limited, England.

The invention also provides an oral dosage form containing a multiparticulate carrier-mediated transport statin formulation as hereinabove defined, in the form of caplets, capsules, particles for suspension prior to dosing, sachets, or tablets. When the dosage form is in the form of tablets, the tablets may be disintegrating tablets, fast dissolving tablets, effervescent tablets, fast melt tablets, and/or mini-tablets. The dosage form can be of any shape suitable for oral administration of a drug, such as spheroidal, cube-shaped oval, or ellipsoidal. The dosage forms can be prepared from the multiparticulates in a manner known in the art and include additional pharmaceutically acceptable excipients, as desired.

Soft Gelatin Capsules

The formulations of the present invention may also be prepared as liquids, which may be filled into soft gelatin capsules. For example, the liquid may include a solution, suspension, emulsion, microemulsion, precipitate, or any other desired liquid media carrying the carrier-mediated transport statin(s). The liquid may be designed to improve the solubility of the carrier-mediated transport statin(s) upon release, or may be designed to form a drug-containing emulsion or dispersed phase upon release. Examples of such techniques are well known in the art. Soft gelatin capsules may be coated, as desired, with a functional coating to delay the release of the drug.

Functional Coatings

All of the particular embodiments described above, including but not limited to, matrix-based, osmotic pump-based, soft gelatin capsules, and/or membrane-controlled forms, which may further take the form of monolithic and/or multi-unit dosage forms, may have a functional coating. Such coatings generally serve the purpose of delaying the release of the drug for a predetermined period. For example, such coatings may allow the dosage form to pass through the stomach without being subjected to stomach acid or digestive juices. For the acid-stable statins used in formulations of the present invention, such protective coatings are not required, but can be used as another way to control the time and place of drug delivery. Thus, such coatings may dissolve or erode upon reaching a desired point in the gastrointestinal tract, such as the upper intestine.

Such functional coatings may exhibit pH-dependent (enteric) or pH-independent (non-enteric) solubility profiles. Those with pH-independent profiles generally erode or dissolve away after a predetermined period, and the period is generally related to the thickness and composition of the coating. Those with pH-dependent profiles, on the other hand, may maintain their integrity while in the acid pH of the stomach, but quickly erode or dissolve upon entering the more basic upper intestine.

Thus, a matrix-based, osmotic pump-based, or membrane-controlled formulation may be further coated with a functional coating that delays the release of the drug. For example, a membrane-controlled formulation may be coated with an enteric coating that delays the exposure of the membrane-controlled formulation until the upper intestine is reached. Upon leaving the acidic stomach and entering the more basic intestine, the enteric coating dissolves. The membrane-controlled formulation then is exposed to gastrointestinal fluid, and then releases at least one carrier-mediated transport statin over an extended period, in accordance with the invention. Examples of functional coatings such as these are well known to those in the art.

In one embodiment, the carrier-mediated transport statin formulations initially delay the release of the drug. Following the delay, the formulation may rapidly release the drug. Such formulations would provide a more rapid and/or immediate therapeutic effect for the subject.

Formulations of the present invention may further comprise pH-modifying agents, for example, agents exhibiting a pKa of from about 1 to about 6.5. Such agents include, but are not limited to, dicarboxylic acids. Dicarboxylic acids include, but are not limited to, 2-ethandioic (oxalic), 3-propandioic (malonic), 4-butandioic (succinic), 5-pentandioic (glutaric), 6-hexandioic (adipic), cis-butenedioic (maleic), trans-butenedioic (fumaric), 2,3-dihydroxybutandioic (tartaric), 2-hydroxy-1,2,3-propanetic carboxylic (citric), pimelic, suberic, azelaic, and sebacic acids. In some embodiments, one or more dicarboxylic acids are included in the formulation.

In some embodiments, the formulation is substantially free from monocarboxylic acids. As used in this context, "substantially free" means that monocarboxylic acids are not added to the formulation, but may be present otherwise. Monocarboxylic acids include, but are not limited to, methanoic (formic), ethanoic (acetic), propanoic (propionic), butanoic (butyric), pentanoic (valeric), hexanoic (caproic), heptanoic (enanthic), 1-hydroxypropanoic (lactic), 3-benzyl-2-propenoic (cinnamic), and 2-oxopropanoic (pyruvic) acids.

The formulations of the present invention may include pH-modifying agents that create a microenvironment around the carrier-mediated transport statin when exposed to aqueous fluids. For example, these agents may create a microenvironment around the carrier-mediated transport statin having a pH of from about 3 to about 6, or, for example, a pH of about 5.

Simply put, the formulations and methods of the present invention deliver a therapeutic dose into the environment of use, which is the small intestine. As it is believed that carrier-mediated transport statin absorption occurs almost entirely in the small intestine, and that absorption from the large intestine is negligible, the methods and formulations of this invention are designed to maximize drug release in the small intestine. Thus, absorption efficiency is maximized, and little drug is wasted.

Unlike acid-instable statins such as pravastatin, acid-stable statins such as atorvastatin and rosuvastatin can be formulated with or without a protective coating. Upon administration to the patient, when no protective coating is applied to the acid-stable statin, the methods and formulations of the present invention generally exhibit an extended release over about 1 to about 6 hours. The formulations and methods of the present invention may also make use of a protective coating, in which case there is generally minimal or no release in the stomach, followed by controlled but complete release into the small intestine.

Thus, some methods and formulations of the present invention completely release at least one carrier-mediated transport statin into the environment of use in less than about six hours. That is, greater than 80% is released by a time prior to about 6 hours following administration. "Completely released" means greater than 80% of the carrier-mediated transport statin in the formulation is released.

Using the compositions of the present invention, the systemic bioavailability of carrier-mediated transport statins can be reduced. For example, the absolute systemic bioavailability from LIPITOR® is about 12% (LIPITOR® package insert (1997) Parke-Davis, Morris Plains N.J.). Using the compositions of the present invention, systemic bioavailability of atorvastatin may be reduced to below about 12%, for example, about 10%, 8%, 5%, or 0%, or any amount less than about 12%. As compared to an equally effective dose of LIPITOR®, or any conventional release atorvastatin formulation, administration of the compositions of the present invention achieves a decrease in the systemic bioavailability to less than about 90%, 80%, 70%, 60%, 50%, 40%, 30%, or 25%, of that of the conventional release formulation. This is referred to herein as the "relative" systemic bioavailability.

Further, for example, the absolute systemic bioavailability from CRESTOR® is about 20% CRESTOR® package insert (2003) AstraZeneca, Wilmington, Del.). Using the compositions of the present invention, systemic bioavailability of rosuvastatin may be reduced to below about 20%, for example, about 18%, 15%, 10%, 5%, or 0%, or any amount less than about 20%. As compared to an equally effective dose of CRESTOR®, or any conventional release rosuvastatin formulation, administration of the compositions of the present invention achieves a decrease in the systemic bioavailability to less than about 90%, 80%, 70%, 60%, 50%, 40%, 30%, or 25%, of that of the conventional release formulation. This is referred to herein as the "relative" systemic bioavailability.

The compositions of the present invention can also be used to increase the liver-specific extraction of carrier-mediated transport statins. For example, hepatic extraction of atorvastatin from LIPITOR® is approximately 70% (Igel et al. (2002) J. Clin. Pharmacol. 42:835). By using the compositions of the present invention, hepatic extraction of atorvastatin may be increased to greater than about 70%, for example to about 75%, 80%, 85%, 90%, 95%, or 100%, or any amount greater than about 70%.

Further, for example, in the case of CRESTOR®, hepatic extraction of rosuvastatin is approximately 90% (Igel et al. (2002) J. Clin. Pharmacol. 42:835). Using the compositions of the present invention, hepatic extraction of rosuvastatin can be increased to greater than about 90%, for example to about 95% or 100%, or any amount greater than about 90%.

The peak plasma concentration, or $C_{max}$, of carrier-mediated transport statins may be reduced by the formulations and compositions of the present invention, as compared to equally effective doses of other carrier-mediated transport conventional release formulations. For example, the $C_{max}$ may be reduced by the formulations and compositions of the present invention as compared to an equally effective dose of LIPITOR®, or any conventional release atorvastatin formulation. For example, as compared to the $C_{max}$ resulting from the use of an equally effective dose of LIPITOR®, or any conventional release atorvastatin formulation, the $C_{max}$ may be reduced to less than about 80%, 70%, 60%, 50%, 40%, 30%, or 25%.

Further, for example, the $C_{max}$ may be re reduced by the formulations and compositions of the present invention as compared to an equally effective dose of CRESTOR®, or any other conventional release rosuvastatin formulation. For example, as compared to the $C_{max}$ resulting from the use of an equally effective dose of CRESTOR®, or any conventional release rosuvastatin formulation, the $C_{max}$ may be reduced to less than about 80%, 70%, 60%, 50%, 40%, 30%, or 25%.

The therapeutic level is the minimum concentration of carrier-mediated transport statin that is therapeutically effective in a particular patient. Of course, one of skill in the art will recognize that the therapeutic level may vary depending on the individual being treated and the severity of the condition.

For example, the age, body weight, and medical history of the individual patient may affect the therapeutic efficacy of the therapy. A competent physician can consider these factors and adjust the dosing regimen to ensure the dose is achieving the desired therapeutic outcome without undue experimentation. It is also noted that the clinician and/or treating physician will know how and when to interrupt, adjust, and/or terminate therapy in conjunction with individual patient response.

The total daily dosage of carrier-mediated transport statin formulations, for example, can range from about 1 mg to about 200 mg. For example, in general, the total daily dosage of atorvastatin in formulations of the present invention ranges from about 1 mg to about 200 mg, about 1 to about 160 mg, about 1 to about 80 mg, about 5 to about 80 mg, about 10 to about 80 mg, or any whole number or fractional amount in between. A single dose may be formulated to contain about 1, 5, 10, 15, 20, 25, 30, 35, 40, 60, 80, 100, 120, 140, 160, 180, or 200 mg of atorvastatin. In one embodiment, a single dose contains about 5, 10, 15, 20, 40, 60, or 80 mg of atorvastatin.

Further, for example, in general, the total daily dosage of rosuvastatin in formulations of the present invention ranges from about 1 mg to about 200 mg, about 1 to about 160 mg, about 1 to about 80 mg, about 5 to about 80 mg, about 10 to about 80 mg, or any whole number or fractional amount in between. A single dose may be formulated to contain about 1, 5, 10, 15, 20, 25, 30, 35, 40, 60, 80, 100, 120, 140, 160, 180, or 200 mg of rosuvastatin. In one embodiment, a single dose contains about 5, 10, 15, 20, 40, 60, or 80 mg of rosuvastatin.

The carrier-mediated transport statin formulations of the present invention may be described by their dissolution profiles. One of skill in the art is familiar with the techniques used to determine such dissolution profiles. The standard methodologies set forth in the U.S. Pharmacopoeia, which methodologies are incorporated herein by reference in relevant part, may be used. For example, the dissolution profile may be measured in either a U.S. Pharmacopoeia Type I Apparatus (baskets) or a U.S. Pharmacopoeia Type II Apparatus (paddles). For pH-independent formulations, the formulations may be tested in phosphate buffer at pH 6.8 or higher, 37° C., and 50-100 rpm. For pH-dependent formulations, the formulations may be tested in 0.01-0.1 N HCl for the first 2 hours at 37° C. and 50-100 rpm, followed by transfer to phosphate buffer at pH 6.8 or higher for the remainder of the test. Other buffer systems suitable for measuring the dissolution profile for pH-dependent and pH-independent formulations are well known to those of skill in the art. For both pH-dependent and pH-independent formulations, surfactants (e.g., 1% sodium lauryl sulfate) may be included in the dissolution media, especially for poorly water-soluble drugs as suggested by the FDA guidelines for in vitro testing of dissolution profiles (http://www.fda.gov/cder/guidance/1306fn-1.pdf).

For example, the in vitro dissolution profile of carrier-mediated transport statin formulations, with no protective coating, of the present invention may correspond to the following:
 (1) about 30% release after about 1-2 hours;
 (2) about 50% release after about 4 hours;
 (3) about 70% release after about 6 hours; and
 (4) greater than about 80% release after about 8 hours.
Alternatively, the profile may correspond to:
 (1) about 20% release after about 1-2 hours;
 (2) about 20% to about 40% release after about 4 hours; and
 (3) greater than about 80% release after about 6 hours.

For formulations of the present invention where no protective coating is used, drug begins releasing immediately in the stomach where there is no initial delay while the drug is in the stomach.

In one embodiment, the formulations of the present invention with no protective coatings may exhibit a release rate, as measured in a Type II dissolution apparatus, in a pH 6.8 buffer, of the following: 1-2 hours: less than about 30%; 4 hours: less than about 60%; 6 hours: less than about 80%; 8-10 hours: greater than about 80%. Such formulations may also exhibit a release rate, as measured in a Type II dissolution apparatus, in a pH 6.8 buffer, of the following: 1-2 hours: less than about 25%; 4 hours: less than about 50%; 8 hours: less than about 80%.

The in vitro dissolution profile of enteric coated carrier-mediated transport statin compositions of the present invention, which may further control bioavailability, may correspond to the following, when tested in acid for 2 hours followed by pH 6.8 or higher buffer:
 (1) minimal release after about 2 hours; and
 (2) complete release after about 8 hours.
Alternatively, the profile may correspond to:
 (1) less than about 50% release after about 2 hours;
 (2) about 20% to about 80% release after about 4 hours; and
 (3) greater than about 60% release after about 6-8 hours.
When an enteric-coating is used, release of the drug from the formulations may be retarded in acid for 1-2 hours. In pH 6.8 or higher buffer, the release of the drug is in a manner consistent with transit into the small intestine, the site of absorption of carrier-mediated transport statins.

The in vitro dissolution profile of non-enteric coated carrier-mediated transport statin compositions of the present invention may correspond to the following:
 (1) minimal release after about 1-2 hours; and
 (2) complete release after about 8 hours.
Alternatively, the profile may correspond to:
 (1) less than about 50% of the carrier-mediated transport statin is released after about 1-2 hours;
 (2) about 20% to about 80% is released after about 4 hours; and
 (3) greater than about 60% is released after about 6-8 hours.

For formulations with non-enteric protective coatings, release of the drug from the formulations is retarded for 1-2 hours, independent of the pH of the dissolution medium. After 1-2 hours, which coincides with emptying of the dosage form from the stomach into the small intestine, the drug is released in a manner consistent with transit of the dosage form through the small intestine, the site of absorption of carrier-mediated transport statins.

Any of the pharmaceutical compositions described above may further comprise one or more pharmaceutically active compounds other than the carrier-mediated transport statins discussed above. Such compounds may be provided to treat the same condition being treated with an carrier-mediated transport statin, or a different one. Those of skill in the art are familiar with examples of techniques for incorporating additional active ingredients into the formulations of the present invention. Alternatively, such additional pharmaceutical compounds may be provided in a separate formulation and co-administered to a patient with an carrier-mediated transport statin composition. Such separate formulations may be administered before, after, or simultaneously with the administration of the carrier-mediated transport statin.

The invention is further illustrated by reference to the following examples. It will be apparent to those skilled in the art that many modifications, both to materials and methods, may be practiced without departing from the purpose and scope of the invention.

EXAMPLES

Example 1

Production of Modified-Release Atorvastatin 10 mg Matrix Tablets Using METHOCEL™ K100LV Premium CR by Direct Compression Modified-release formulations of atorvastatin, comprising the components set forth in Table 1, are produced as follows.

TABLE 1

| Ingredient | Function | Qty % (w/w) | Qty % (w/w) | Qty % (w/w) |
|---|---|---|---|---|
| Atorvastatin | Active | 5.00 | 5.00 | 5.00 |
| Lactose | Diluent | 45.58 | 30.78 | 20.78 |
| AVICELL ™ PH101 | Dry Binder/diluent | 28.72 | 23.52 | 13.52 |
| METHOCEL ™ K100LV Premium CR | Controlled-Release Polymer | 20.00 | 40.00 | 60.00 |
| Colloidal Silicon Dioxide | Glidant | 0.20 | 0.20 | 0.20 |
| Magnesium Stearate | Lubricant | 0.50 | 0.50 | 0.50 |
| Total | | 100 | 100 | 100 |

Each ingredient is first weighed. The lactose, atorvastatin, colloidal silicon dioxide, METHOCEL™, and AVICELL™ are placed in a blender and mixed for 15 minutes until homogenous. The magnesium stearate is then added to the blender and the mixture is mixed for an additional 5 minutes. The mixture is compressed into oval tablets on a suitable tablet machine. The target weight of each tablet is 200 mg.

Example 2

Production of Modified-Release Atorvastatin 10 mg Matrix Tablets Using METHOCEL™ K100M Premium CR and Sodium Lauryl Sulfate by Direct Compression Modified-release formulations of atorvastatin as set forth in Table 2 are produced as follows.

TABLE 2

| Ingredient | Function | Qty % (w/w) | Qty % (w/w) | Qty % (w/w) |
|---|---|---|---|---|
| Atorvastatin | Active | 5.00 | 5.00 | 5.00 |
| Lactose | Diluent | 45.58 | 30.78 | 20.78 |
| AVICELL ™ PH101 | Dry Binder/Diluent | 27.72 | 22.52 | 12.52 |
| Sodium Lauryl Sulphate | Surface Active Agent | 1.00 | 1.00 | 1.00 |
| METHOCEL ™ K100M Premium CR | Controlled-Release Polymer | 20.00 | 40.00 | 60.00 |
| Colloidal Silicon Dioxide | Glidant | 0.20 | 0.20 | 0.20 |
| Magnesium Stearate | Lubricant | 0.50 | 0.50 | 0.50 |
| Total | | 100 | 100 | 100 |

Each ingredient is first weighed. The lactose, atorvastatin, sodium lauryl sulphate, colloidal silicon dioxide, METHOCEL™, and AVICELL™ are placed in a blender and mixed for 15 minutes until homogenous. The magnesium stearate is then added to the blender and the mixture is mixed for an additional 5 minutes. The mixture is compressed into oval tablets on a suitable tablet machine. The target weight of each tablet is 200 mg.

Example 3

Production of Modified-Release Atorvastatin 5 mg Matrix Tablets Using METHOCEL™ K100LV Premium CR by Wet Granulation Modified-release formulations of atorvastatin as set forth in Table 6 are produced as follows.

TABLE 3

| Ingredient | Function | Qty % (w/w) | Qty % (w/w) | Qty % (w/w) |
|---|---|---|---|---|
| Atorvastatin | Active | 5.00 | 5.00 | 5.00 |
| Lactose | Diluent | 45.58 | 30.78 | 20.78 |
| AVICELL ™ PH101 | Dry Binder/Diluent | 23.72 | 18.52 | 8.52 |
| METHOCEL ™ K100LV Premium CR | Controlled-Release Polymer | 20.00 | 40.00 | 60.00 |
| Colloidal Silicon Dioxide | Glidant | 0.20 | 0.20 | 0.20 |
| Magnesium Stearate | Lubricant | 0.50 | 0.50 | 0.50 |
| Polyvinyl Pyrrolidone | Binder | 5.0 | 5.0 | 5.0 |
| Isopropyl Alcohol | Solvent | N/A | N/A | N/A |
| Total | | 100 | 100 | 100 |

Each ingredient is first weighed. The atorvastatin is then dissolved in the isopropyl alcohol (IPA). The polyvinyl pyrrolidone (PVP) is then dissolved in the IPA/atorvastatin solution. Then, 50% of the Avicel and 50% of the lactose are placed in a suitable mixer, such as a planetary mixer (Hobart) or a high shear mixer (Diosna/Fielder), and blended for 15 minutes to produce a homogenous mixture. While continuing to mix the solution, the atorvastatin/PVP solution, which serves as the granulating fluid, is added. Mixing is continued until a suitable granulation end point is reached, adding more isopropyl alcohol if necessary to produce a suitable granule. The granules are then dried (using either an oven or fluidization equipment) until they contain an acceptable level of moisture (e.g., less than about 1.0%) and an acceptable isopropyl alcohol content (e.g., less than about 0.5%). The dry granulate is then passed through suitable comminution equipment (e.g., Co-Mill, Fitzpatrick mill) that has been fitted with a suitably sized screen (e.g., 100-500 microns). The resulting granulate is then placed in a blender to which the colloidal silicon dioxide, and the remainder of the Avicel and lactose are added and mixed for 15 minutes. The magnesium stearate is then added and blended for an additional 5 minutes. The mixture is then compressed into oval shaped tablets using a suitable tablet machine. The target weight of each tablet is 100 mg. Alternatively, the PVP can be dissolved in the isopropyl alcohol and the atorvastatin added prior to the drying and granulation process described above. Another alternative is to dissolve the atorvastatin in the isopropyl alcohol (or any suitable solvent) and the PVP is then added prior to the drying and granulation process described above.

Example 4

Production of Modified-Release Atorvastatin 5 mg Matrix Tablets Using METHOCEL™ K100M Premium CR, Sodium Caprate, and Sodium Lauryl Sulfate by Wet Granulation Modified-release formulations of atorvastatin as set forth in Table 4 are produced according to the process of Example 3, with the addition of sodium lauryl sulfate and sodium caprate to the initial mixture of lactose and AVICELL™. Alternatively, the sodium lauryl sulphate and sodium caprate can be added after the granulated mixture is obtained.

TABLE 4

| Ingredient | Function | Qty % (w/w) | Qty % (w/w) | Qty % (w/w) |
|---|---|---|---|---|
| Atorvastatin | Active | 5.00 | 5.00 | 5.00 |
| Lactose | Diluent | 25.58 | 15.78 | 10.78 |
| AVICELL ™ PH101 | Dry Binder/Diluent | 12.72 | 12.52 | 7.52 |
| METHOCEL ™ K100M Premium CR | Controlled-Release Polymer | 20.00 | 40.00 | 60.00 |
| Sodium Caprate | Permeability Enhancer | 30.00 | 20.00 | 10.00 |
| Sodium Lauryl Sulfate | Surfactant | 1.00 | 1.00 | 1.00 |
| Colloidal Silicon Dioxide | Glidant | 0.20 | 0.20 | 0.20 |
| Magnesium Stearate | Lubricant | 0.50 | 0.50 | 0.50 |
| Polyvinyl Pyrrolidone | Binder | 5.0 | 5.0 | 5.0 |
| Isopropyl Alcohol | Solvent | N/A | N/A | N/A |
| Total |  | 100 | 100 | 100 |

For Examples 1-4, in vitro dissolution tests are performed on the atorvastatin modified release core tablets using the following parameters: USP (711); paddle @ 50 RPM; media: phosphate buffer, pH 6.8; a suitable surfactant, (e.g., 1% sodium lauryl sulphate) and UV absorbance at appropriate wavelength.

Example 5

Rapid-Release Tablet Core of 10 mg Rosuvastatin

Rapid-release tablet cores of rosuvastatin, comprising the components set forth in Table 5, are produced as follows. These cores may be used in membrane-controlled formulations.

TABLE 5

| Ingredient | Function | Qty % (w/w) | Qty % (w/w) | Qty % (w/w) | Qty % (w/w) |
|---|---|---|---|---|---|
| Rosuvastatin | Active | 10.00 | 10.00 | 10.00 | 10.00 |
| Lactose Anhydrous (direct compression grade) | Diluent | 79.50 | 67.13 | 44.75 | 22.37 |
| Microcrystalline Cellulose (AVICELL ™ PH200) | Dry Binder/Diluent | 10.00 | 22.37 | 44.75 | 67.13 |
| Magnesium Stearate | Lubricant | 0.5 | 0.5 | 0.5 | 0.5 |
| Total |  | 100.00 | 100.00 | 100.00 | 100.00 |

Each ingredient is weighed using a suitable balance. The AVICELL™, rosuvastatin, and lactose are mixed in a V-type blender for 30 minutes until a homogenous mixture is achieved. The magnesium stearate is added and the ingredients are mixed for an additional 5 minutes. The mixture is then divided and compressed into tablets on a suitable tablet machine using plain oval tooling. The target weight of each tablet is 100 mg.

Example 6

Membrane Coating of Rapid-Release Tablets of Rosuvastatin (Membrane Controlled)

The rosuvastatin formulations set forth in Example 5 above are coated with the coatings described in Table 6.

TABLE 6

| Ingredient | mg/tab | mg/tab | mg/tab |
|---|---|---|---|
| Polymer | 11.00 | 9.20 | 11.00 |
| Sucrose | 29.00 | 17.00 | 21.00 |
| Citrate | 2.00 | 1.60 | 1.90 |
| Castor Oil Polymerized | 1.00 | 1.2 | 1.4 |
| Sodium Hydrogen Carbonate | 1.00 | 1.00 | 1.00 |
| Acetone# | N/A | N/A | N/A |

Polymer = terpolymer of polyvinyl chloride, polyvinyl acetate, and polyvinyl alcohol (PVC/PVAc/PVOH)
Solvent is removed during processing.

The tablets from Example 5 are placed in a suitable coating machine (e.g., Acelacota) and heated to the required temperature. A sufficient amount of the polymer solution indicated in Table 6 is then sprayed onto the tablets, and the tablets are dried in the coating machine.

In vitro dissolution tests are performed on the rosuvastatin modified-release membrane-controlled formulations using the following parameters: USP (711); paddle @ 50 RPM; media: phosphate buffer, pH 6.8; and UV absorbance at appropriate wavelength.

Example 7

Enteric-Coated Membrane Tablets

Any of the dosage forms according to the present invention may be coated with an enteric coating suspension. In order to determine the amount of enteric coating required on the modified-release tablets, coating experiments are carried out. The coating trial is carried out on a selected 10 mg strength formulation prototype (approximately 1-2 kg batch size).

Composition details for enteric-coating suspension:

TABLE 7

| Ingredient | Qty % (w/w) | Qty/Tab (mg) |
|---|---|---|
| EUDRAGIT ™ L30 D55 (solid content) | 4.0 | TBD |
| Talc, USP | 2.0 | TBD |
| Triethyl Citrate | 0.4 | TBD |
| Purified Water | 93.6 | N/A |
| Total | 100.0 |  |

The coating is applied to the membrane-coated tablets using EUDRAGIT™ L30 D55, at 5%, 10%, 15%, and 20% of coating polymer thickness (i.e., percentage weight gain on the tablet coat). The coating is applied onto the membrane-coated tablet cores using suitable coating equipment.

In vitro dissolution tests are performed on enteric-coated modified-release tablets using the following parameters: USP (711); paddle @ 50 RPM; media: 0.01 to 0.1 N HCl for 2 hours, followed by phosphate buffer, pH 6.8 or higher, for the remainder of the test; UV absorbance at appropriate wavelength.

Samples are collected and subjected to dissolution testing. The target in vitro dissolution for enteric-coated tablets is shown below:

| Media | Time point (Hour) | % Released |
|---|---|---|
| Acid | 2.0 | ≤10% |
| pH 6.8 | 1.0 | 10–40 |
| Buffer | 2.0 | 30–70 |
|  | 3.0 | ≥45 |
|  | 4.0 | ≥60 |
|  | 5.0 | ≥75 |
|  | 6.0 | ≥80 |

Example 8 pH-Independent Functional Coating Formulations

Any of the dosage forms according to the present invention may be coated with a pH-independent coating, for example, as provided in Table 8 below.

| Ingredient | Function | g/Batch |
|---|---|---|
| EUDRAGIT ™ RS 30D | Polymer | 200.00 |
| Talc | Anti-adherent | 60.00 |
| Triethyl Citrate | Plasticizer | 12.00 |
| Simethicone Emulsion | Dispersant | 1.00 |
| Water | Solvent | 392.00 |
| Total |  | 665 |

In vitro dissolution tests are performed on pH-independent functional coated modified-release tablets using the following parameters: USP (711); paddle @ 50 RPM; media: phosphate buffer, pH 6.8; and UV absorbance at appropriate wavelength.

The target in vitro dissolution for pH-independent functional coated tablets is shown below:

| Media | Time point (Hour) | % Released |
|---|---|---|
| pH 6.8 | 1.0 | ≤10% |
| Buffer | 2.0 | 10–40% |
|  | 3.0 | 30–70% |
|  | 4.0 | ≥45% |
|  | 5.0 | ≥60% |
|  | 6.0 | ≥75% |
|  | 7.0 | ≥80% |

Example 9

Comparison of Modified-Release Atorvastatin Formulation and Conventional Release Atorvastatin Formulation in Lowering Cholesterol in a Patient To evaluate the efficacy of the modified-release formulations of the present invention, the formulations are tested for reduction of cholesterol in patients with primary hypercholesterolemia and mixed dyslipidemia, and compared to LIPITOR® at the same dose. Low doses are also tested to show that the present formulations are more effective at lower doses than LIPITOR®. The present formulations are also tested for their effect on systemic ubiquinone depletion relative to the depletion caused by LIPITOR®. Results will show that the present formulations cause significantly less systemic ubiquinone depletion relative to conventional release formulations of atorvastatin, such as LIPITOR®.

The study begins with at least a four-week placebo period, where patients receive dietary advice. Patients are randomized into groups that receive:

A. Conventional atorvastatin (LIPITOR®) at 20 mg daily for 6 weeks, subsequently increased to 40 mg daily for 6 weeks;

B. Inventive formulation at 5 mg daily for 6 weeks. At the end of that period, patients are randomized to receive either 5 mg or 10 mg daily for an additional 6 weeks;

C. Inventive formulation at 10 mg daily for 6 weeks. At the end of that period, patients are randomized to receive either 10 mg or 20 mg daily for an additional 6 weeks; or D. Inventive formulation at 20 mg for 6 weeks, subsequently increased to 40 mg daily for 6 weeks.

Groups A and D each contain 20 patients, while Groups B and C each contain 40 patients, to permit randomization into groups of 20 patients at week 6. This design permits a placebo period, and a dose-response comparison of the present formulations with the conventional product.

Cholesterol levels are measured prior to study entry, prior to randomization (baseline), and at weeks 3, 6, 9, and 12. Systemic ubiquinone levels are measured prior to randomization, and at weeks 6 and 12, to determine the relative depletion of systemic ubiquinone levels. Baseline liver enzymes are measured at weeks 3, 6, 9, and 12. Atorvastatin plasma concentrations for population analysis are obtained at weeks 6 and 12.

Efficacy endpoints include the change from baseline in total cholesterol (C), LDL-C, Triglycerides (TG), HDL-C, VLDL-C and the Total-C/HDL-C and LDL-C/HDL-C ratios. Safety will be assessed by considering, among other things, the change from baseline in systemic ubiquinone levels, and the change from baseline in liver transaminase enzymes.

Example 10

Comparison of Modified-Release Rosuvastatin Formulation and Conventional Release Rosuvastatin Formulation in Lowering Cholesterol in a Patient To evaluate the efficacy of the modified-release formulations of the present invention, the formulations are tested for reduction of cholesterol in patients with primary hypercholesterolemia and mixed dyslipidemia, and compared to CRESTOR® at the same dose. Low doses are also tested to show that the present formulations are more effective at lower doses than CRESTOR®. The present formulations are also tested for their effect on systemic ubiquinone depletion relative to the depletion caused by CRESTOR®. Results will show that the present formulations cause significantly less systemic ubiquinone depletion relative to conventional release formulations of rosuvastatin, such as CRESTOR®.

The study begins with at least a four-week placebo period, where patients receive dietary advice. Patients are randomized into groups that receive:

A. Conventional rosuvastatin (CRESTOR®) at 10 mg daily for 6 weeks, subsequently increased to 20 mg daily for 6 weeks;

B. Inventive formulation at 2.5 mg daily for 6 weeks. At the end of that period, patients are randomized to receive either 2.5 mg or 5 mg daily for an additional 6 weeks;

C. Inventive formulation at 5 mg daily for 6 weeks. At the end of that period, patients are randomized to receive either 5 mg or 10 mg daily for an additional 6 weeks; or D. Inventive formulation at 10 mg for 6 weeks, subsequently increased to 20 mg daily for 6 weeks.

Groups A and D each contain 20 patients, while Groups B and C each contain 40 patients, to permit randomization into groups of 20 patients at week 6. This design permits a placebo period, and a dose-response comparison of the present formulations with the conventional product.

Cholesterol levels are measured prior to study entry, prior to randomization (baseline), and at weeks 3, 6, 9, and 12. Systemic ubiquinone levels are measured prior to randomization, and at weeks 6 and 12, to determine the relative depletion of systemic ubiquinone levels. Baseline liver enzymes are measured at weeks 3, 6, 9, and 12. Rosuvastatin plasma concentrations for population analysis are obtained at weeks 6 and 12.

Efficacy endpoints include the change from baseline in total cholesterol (C), LDL-C, Triglycerides (TG), HDL-C, VLDL-C and the Total-C/HDL-C and LDL-C/HDL-C ratios. Safety will be assessed by considering, among other things, the change from baseline in systemic ubiquinone levels, and the change from baseline in liver transaminase enzymes.

What is claimed is:

1. A method of increasing the hepatic bioavailability of atorvastatin, or a pharmaceutically acceptable salt thereof, comprising administering to a subject a therapeutically effective amount of atorvastatin, or a pharmaceutically acceptable salt thereof, in a pharmaceutical formulation, wherein the formulation is a matrix-based tablet comprising:
    (a) atorvastatin, or a pharmaceutically acceptable salt thereof,
    (b) dimethyl sulfoxide,
    (c) sodium lauryl sulfate, and
    (d) polyvinyl pyrrolidone,
wherein (a), (b), (c), and (d) are compressed into a polymer matrix comprising hydroxypropylmethyl cellulose and wherein the formulation releases atorvastatin, or a pharmaceutically acceptable salt thereof, at a rate that avoids saturating the intestinal and hepatocytic transport mechanisms.

2. The method of claim 1, wherein the formulation releases greater than about 80% of its atorvastatin content over a period of from about 1 hours to about 8 hours.

3. The method of claim 1, wherein the administration achieves a relative systemic bioavailability of atorvastatin, or a pharmaceutically acceptable salt thereof, as compared to an equally effective dose of a conventional release formulation, of less than about 90%.

4. The method according to claim 1, wherein the administration achieves a relative systemic bioavailability of atorvastatin, or a pharmaceutically acceptable salt thereof, as compared to an equally effective dose of a conventional release formulation, of less than about 80%.

5. A method of treating hypercholesterolemia comprising administering to a subject in need of such treatment, a therapeutically effective amount of atorvastatin, or a pharmaceutically acceptable salt thereof, in a pharmaceutical formulation, wherein the formulation is a matrix-based tablet comprising:
    (a) atorvastatin, or a pharmaceutically acceptable salt thereof,
    (b) dimethyl sulfoxide,
    (c) sodium lauryl sulfate, and
    (d) polyvinyl pyrrolidone,
wherein (a), (b), (c), and (d) are compressed into a polymer matrix comprising hydroxypropylmethyl cellulose and wherein the formulation releases atorvastatin, or a pharmaceutically acceptable salt thereof, over a period of greater than about 2 hours.

6. The method of claim 5, wherein the formulation exhibits an atorvastatin release rate as follows: 2 hours: less than or equal to about 40%; 4 hours: between about 20% and about 80%; and 6 hours: greater than about 70%.

7. A modified-release formulation, wherein the formulation is a matrix-based tablet comprising:
    (a) atorvastatin, or a pharmaceutically acceptable salt thereof,
    (b) dimethyl sulfoxide,
    (c) sodium lauryl sulfate, and
    (d) polyvinyl pyrrolidone,
wherein (a), (b), (c), and (d) are compressed into a polymer matrix comprising hydroxypropylmethyl cellulose and wherein the formulation releases atorvastatin, or a pharmaceutically acceptable salt thereof, at a rate that is about equal to or less than the rate of absorption in the intestine and in the liver.

8. The formulation according to claim 7, wherein the formulation exhibits an atorvastatin release rate as follows: 2 hours: less than or equal to about 40%; 4 hours: between about 20% and about 80%; and 6 hours: greater than about 70%.

* * * * *